United States Patent [19]

Inazu et al.

[11] Patent Number: 5,391,552
[45] Date of Patent: Feb. 21, 1995

[54] DIPHENYLPIPERAZINE DERIVATIVE AND DRUG FOR CIRCULATORY ORGAN CONTAINING THE SAME

[75] Inventors: Masato Inazu; Yoshiyuki Miyata; Toshihiro Morimoto; Takeshi Yamamoto; Yuji Yoshiko; Kazunori Harada; Yoshiharu Momota; Masayuki Yanagi; Ryoko Yokota; Tetsuo Katoh; Takayuki Namiki; Makoto Kimura; Nobuyuki Kawakatsu, all of Yokohama, Japan

[73] Assignee: Pola Chemical Industries, Inc., Shizuoka, Japan

[21] Appl. No.: 988,911

[22] PCT Filed: Sep. 13, 1991

[86] PCT No.: PCT/JP91/01227
 § 371 Date: May 10, 1993
 § 102(e) Date: May 10, 1993

[87] PCT Pub. No.: WO92/05165
 PCT Pub. Date: Apr. 2, 1992

[30] Foreign Application Priority Data

Sep. 13, 1990 [JP] Japan .................... 2-243526

[51] Int. Cl.$^6$ ............... A61K 31/495; C07D 295/088
[52] U.S. Cl. ................... 514/255; 544/374; 544/396; 549/552; 549/555; 549/559
[58] Field of Search ............... 544/396; 514/255

[56] References Cited

FOREIGN PATENT DOCUMENTS

| 0025111 | 3/1981 | European Pat. Off. |
| 0229623 | 7/1987 | European Pat. Off. |
| 3200304A1 | 8/1982 | Germany |
| 3723648A1 | 1/1989 | Germany |
| WO90/00331 | 4/1990 | WIPO |

OTHER PUBLICATIONS

Godfraind et al., *Pharmacological Reviews*, vol. 38, No. 4, 1986, pp. 321–381.
Holmes et al., *Drugs*, vol. 27, 1984, pp. 6–44.
Toyoda et al., *Journal of the Neurological Sciences*, vol. 25, 1975, pp. 371–375.
Godfraind et al., *Drugs of Today*, vol. 18, No. 1, 1982, pp. 27–42.

*Primary Examiner*—Emily Bernhardt
*Attorney, Agent, or Firm*—Bacon & Thomas

[57] ABSTRACT

A diphenylpiperazine derivative represented by general formula (1), salt thereof, and drug for the circulatory organs containing the same as the active ingredient:

$$\text{(1)}$$

wherein $R^1$ and $R^2$ may be the same or different from each other and each represents hydrogen, halogen, alkyl, alkoxy, nitro, amino, hydroxy, optionally esterified carboxyl or trifluoromethyl; $R^3$ represents hydrogen, alkyl, aralkyl, acyl, nitro or optionally esterified carboxymethyl; Ar represents phenyl or naphthyl which may have one to three substituents such as halogen, alkyl, alkoxy, aryloxy, aralkyloxy, nitro, amino, cyano, acyl, hydroxy, optionally esterified carboxyl, substituted sulfonyl, aryl or trifluoromethyl; Z represents sulfur or -$NR^4$- wherein $R^4$ represents hydrogen, alkyl, aralkyl, acyl, aryl, substituted sulfonyl or optionally esterified carboxyl; m represents a number of 1 to 5; and n represents a number of 0 to 5.

9 Claims, No Drawings

DIPHENYLPIPERAZINE DERIVATIVE AND DRUG FOR CIRCULATORY ORGAN CONTAINING THE SAME

TECHNICAL FIELD

The present invention relates to a novel diphenylpiperazine derivative or its salts having a strong antagonism against calcium, and to a drug for circulatory organs containing the diphenylpiperazine derivative or its salts for use in the cure and prevention of a variety of circulatory organ diseases.

BACKGROUND ART

Conventionally, a variety of drugs have been developed and clinically used for the cure and prevention of circulatory organ diseases. Among them, an antagonism against calcium particularly inhibits inflow of calcium ions into cells, which is caused by excitation of a cell membrane of cardiac muscle or vascular smooth muscle, controls contraction of such muscle and promotes vasodilation. A calcium antagonist, therefore, is useful for the cure and prevention of hypertension, angina pectoris, cerebral circulatory disturbances and the like.

As typical examples of such a calcium antagonism, furnarizine clinically applied as a cerebral circulation accelerator, cinnarizine clinically applied as an angiotelectasis agent, and the like are known. However, development of a new medicament, which has an antagonism against calcium with less side effect, has still been desired.

Accordingly, an object of the present invention is to provide a novel compound which possesses an excellent antagonism against calcium and is useful as a drug, and a drug containing this compound for circulatory organs.

Under such circumstances, the present inventors have carried out extensive studies and have found that a novel diphenylpiperazine derivative represented by general formula (1) as described hereinafter and its salts possess a strong antagonism against calcium compared with furnarizine or cinnarizine conventionally used, a less toxicity and a high safety and is widely applicable as a drug for circulatory organs.

DISCLOSURE OF INVENTION

An object of the present invention is to provide a diphenylpiperazine derivative represented by the following general formula (1) or its salts and a drug for circulatory organs, containing this compound as an active ingredient:

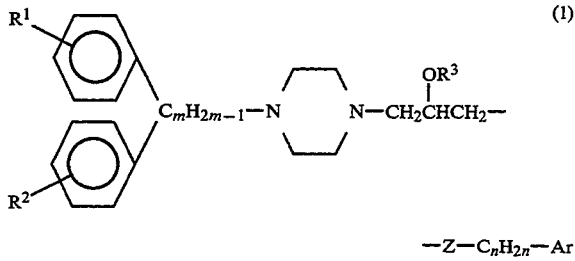

(1)

[wherein, $R^1$ and $R^2$ are the same or different and independently represent a hydrogen atom, a halogen atom, an alkyl group, an alkoxy group, a nitro group, an amino group, a hydroxy group, an optionally esterified carboxyl group or a trifluoromethyl group; $R^3$ represents a hydrogen atom, an alkyl group, an aralkyl group, an acyl group, a nitro group or an optionally esterified carboxymethyl group; Ar represents a phenyl or naphthyl group which may have 1 to 3 substituents such as halogen, alkyl, alkoxy, aryloxy, aralkyloxy, nitro, amino, cyano, acyl, hydroxy, optionally esterified carboxyl, substituted sulfonyl, aryl or trifluoromethyl; Z represents a sulfur atom or a group of $-NR^4-$ ($R^4$ represents a hydrogen atom, an alkyl group, an aralkyl group, an acyl group, an aryl group, a substituted sulfonyl group or an optionally esterified carboxyl group); m represents a number of 1 to 5; and n represents a number of 0 to 5.

BEST MODE FOR CARRYING OUT THE INVENTION

In the general formula (1), examples of the halogen atom include a fluorine atom, chlorine atom, iodine atom, bromine atom. Examples of the alkyl group include groups having 1 to 10 carbon atoms such as methyl, ethyl, propyl, isopropyl, butyl, isobutyl, sec-butyl, tert-butyl, pentyl, isopentyl, neopentyl, hexyl, octyl, nonyl, decyl, cyclopentyl, and cyclohexyl. Examples of the alkoxyl group include groups having 1 to 8 carbon atoms such as methoxyl, ethoxyl, propoxy, isopropoxy, butoxy, pentyloxy, hexyloxy, cyclopentyloxy and cyclohexyloxy. Examples of the optionally esterified carboxyl group include alkoxycarbonyl groups such as methoxycarbonyl, ethoxycarbonyl, propyloxycarbonyl, and butyloxycarboxyl. Examples of the optionally esterified carboxymethyl group include methoxycarbonylmethyl, ethoxycarbonylmethyl and carboxylmethyl. Examples of the aralkyl group include benzyl, phenylethyl, methylbenzyl and naphthylmethyl. Examples of the acyl group include alkanoyl groups such as acetyl, propionyl and butyryl, and aroyl groups such as benzoyl, halogenobenzoyl and alkoxybenzoyl. Examples of the aryl group include a phenyl which may have one or more substituents (such as halogen, alkyl, alkoxyl, hydroxy, amino and the like). Examples of the aryloxyl group include a phenoxyl group. Examples of the aralkyloxyl group include a benzyloxy group. Examples of the substituted sulfonyl group include a methanesulfonyl group and p-toluenesulfonyl group.

Among these groups, particularly preferable groups for $R^1$ and $R^2$ are hydrogen and halogen, and for $R^3$, hydrogen, alkyl, alkanoyl, nitro or benzyl.

Salts of the diphenylpiperazine derivatives represented by the general formula (1) are not particularly limited so far as they are pharmacologically acceptable, and, for example, acid addition salts and quaternary ammonium salts are mentioned. In order to form a acid addition salt, organic and inorganic acids can be used. Examples of organic acid include acetic acid, fumaric acid, maleic acid, citric acid, malonic acid and sufonic acids such as methylsulfonic acid and p-toluensulfonic acid. Examples of inorganic acid include hydrochloric acid, sulfuric acid, nitric acid, phosphoric acid and boric acid. Examples of compounds useful for forming a quaternary ammonium salt include alkyl halides such as methyl chloride, methyl bromide, methyl iodide, and alkylsulfuric acids such as methylsulfuric acid and dimethylsulfuric acid.

As to particularly preferable examples of the diphenylpiperazine derivative represented by the general formula (1), the following compounds and their salts are given:

1-diphenylmethyl-4-(2-hydoxy-3-phenylthiopropyl)piperazine, 1-[4,4-bis(4-fluorophenyl)butyl]-4-(2-hydroxy-3-phenylthiopropyl)piperazine, 1-[4,4-bis(4-fluorophenyl)butyl]-4-(2-methoxy-3-phenylthiopropyl)piperazine, 1-(2-acetoxy-3-phenylthiopropyl)-4-[4,4-bis(4-fluorophenyl)butyl]piperazine, (S)-(−)-1-[4,4-bis(4-fluorophenyl)butyl]-4-(2-hydroxy-3-phenylthiopropyl)piperazine, (R)-(+)-1-[4,4-bis(4-fluorophenyl)butyl]-4-(2-hydroxy-3-phenylthiopropyl)piperazine, 1-[4,4-bis(4-fluorophenyl)butyl]-4-[2-hydroxy-3-(4-methylphenylthio)propyl]-piperazine, 1-[2-hydroxy-(4-aminophenylthio)propyl]4-[4,4-bis(4-fluorophenyl)butyl]piperazine, 1-[bis(4-fluorophenyl)methyl]-4-(2-hydroxy-3phenylmethylthiopropyl)piperazine, 1-[3,3-bis(4-fluorophenyl)propyl]-4-(2-hydroxy-3-phenylthiolpropyl)piperazine, 1-[4,4-bis(4-fluorophenyl)butyl]-4-(2-hydroxy-3-phenylmethylthiolpropyl)piperazine, 1-[4,4-bis(4-fluorophenyl)butyl]-4-[3-(4-chlorophenylthio)-2-hydroxypropyl]piperazine, 1-[4,4-bis(4-fluorophenyl)-butyl]-4-[3-(3,4-dichlorophenylthio)-2-hydroxypropyl]piperazine, 1-[4,4-bis(4-fluorophenyl)butyl]-4-[2-hydroxy-3-(2-methoxyphenylthio)propyl]piperazine, 1-[4,4-bis(4-fluorophenyl)butyl]-4-[3-(4-fluorophenylthio)-2-hydroxypropyl]piperazine, 1-[4,4-bis(4-fluorophenyl)butyl]-4-[2-hydroxy-3-(4-hydroxyphenylthio)propyl]piperazine, 1-[4,4-bis(4-fluorophenyl)butyl]-4-[2-hydroxy-3-(4-methoxyphenylthio)propyl]piperazine, 1-[4,4-bis(4-fluorophenyl)butyl]-4-[2-hydroxy-3-(3-methoxyphenylthio)propyl]piperazine, 1-[bis(4-fluorophenyl)methyl]-4-[2-hydroxy-3-(2-methoxyphenylthio)propyl]piperazine, 1-(2,2-diphenylethyl)-4-(2-hydroxy-3-phenylthiopropyl)piperazine, 1-(3,3-diphenylpropyl)-4-(2-hydroxy-3-phenylthiopropyl)piperazine, 1-(4,4-diphenylbutyl)-4-(2-hydroxy-3-phenylthiopropyl)piperazine, 1-[bis(4-fluorophenyl)methyl]-4-(2-hydroxy-3-phenylthiopropyl)piperazine, 1-[bis(4-fluorophenyl)methyl-4-[2-hydroxy-3-(4-methoxyphenylthio)propyl]piperazine, 1-[4,4-bis(4-fluorophenyl)butyl]-4-[2-hydroxy-3-(1-naphthylthio)propyl]piperazine, 1-[4,4-bis(4-fluorophenyl)butyl]-4-[2-hydroxy-3-(2,3,4-trimethoxyphenylthio)propyl]piperazine, 1-[4,4-bis(4-fluorophenyl)butyl]-4-[3-(3,4-dimethoxyphenylthio)-2-hydoxypropyl]piperazine, 1-[4,4-bis(4-fluorophenyl)butyl]-4-[2-hydroxy-3-(3,5-di-tert-butyl-4-hydroxyphenylthio) propyl]piperazine, 1-diphenylmethyl-4-(2-hydroxy-3-phenylthiopropyl)piperazine, 1-diphenylmethyl-4-[2-hydroxy-3-(2-phenylthio)propyl]piperazine, 1-diphenylmethyl-4-[2-hydroxy-3-{2-(2-methoxyphenyl)ethylthio}propyl]piperazine, 1-[3-{2-(3,4-dimethoxyphenyl)ethylthio}-2-hydroxypropyl]-4-diphenylmethylpiperazine, 1-[4,4-bis(4-fluorophenyl)butyl]-4-[2-hydroxy-3-(2-phenylethylthio)propyl]piperazine, 1-[4,4-bis(4-fluorophenyl)-butyl]-4-(2-nitroxypropyl-3-phenylthio)piperazine, 1-[4,4-bis(4-fluorophenyl)butyl]-4-(2-benzyloxypropyl-3-phenylthio)piperazine, 1-[4,4-bis(4-fluorophenyl)butyl]-4-[2-hydroxy-3-(4-nitrophenylthio)propyl]piperazine, 1-[4,4-bis(4-fluorophenyl)butyl]-4-[2-hydroxy-3-(3-phenylpropylthio)propyl]piperazine, 1-[4,4-bis(4-fluorophenyl)butyl]-4-[3-(4-chlorophenylmethylthio)-2-hydroxypropyl]piperazine, 1-[4,4-bis(4-fluorophenyl)-butyl]-4-[3-(3,4-dichlorophenylmethylthio)-2-hydroxypropyl]piperazine, 1-[4,4-bis(4-fluorophenyl)butyl]-4-[2-hydroxy-3-(4-methylphenylmethylthio)propyl]piperazine, 1-[4,4-bis(4-fluorophenyl)butyl]-4-[2-hydroxy-3-(4-methoxyphenylmethylthio)propyl]piperazine, 1-[4,4-bis(4-fluorophenyl)butyl]-4-[3-(2,3-dimethoxyphenylmethylthio)-2-hydroxypropyl]piperazine, 1-[4,4-bis(4-fluorophenyl)butyl]4-[2-hydroxy-3-(2,3,4-trImethoxyphenylmethylthio)propyl]piperazine, 1-diphenylmethyl-4-(2-hydroxy-3-phenylaminopropyl)piperazine, 1-[4,4-bis(4-fluorophenyl)butyl]-4-(2-hydroxy-3-phenylamlnopropyl]piperazine, 1-[4,4-bis(4-fluuorophenyl)butyl]-4-[2-methoxy-3-(N-methyl-N-phenylamino)propyl]piperazine, 1-[4,4-bis(4-fluorophenyl)butyl]-4-[2-acetoxy-3-(N-acetyl-N-phenylamino)propyl]piperazine, 1-[4,4-bis(4-fluorophenyl)butyl]-4-[3-(N-methyl-N-phenylamino)-2-phenylmethyloxypropyl]piperazine, (S)-(−)-1-[4,4-bis(4-fluorophenyl)butyl]-4-(2-hydroxy-3-phenylaminopropyl)piperazine, (R)-(+)-1-[4,4-bis(4-fluorophenyl)butyl]-4-(2-hydroxy-3-phenylaminopropyl)piperazine, 1-[4,4-bis(4-fluorophenyl)butyl]-4-[2-hydroxy-3-(4-methylphenylamino)propyl]piperazine, 1-[(4-aminophenylamino)-2-hydroxypropyl]-1-[4,4-bis(4-fluorophenyl)butyl]piperazine, 1-[bis(4-fluorophenyl)methyl]-4-(2-hydroxy-3-phenylmetylaminopropyl)piperazine, 1-[3,3-bis(4-fluorophenyl)propyl]-4-(2-hydroxy-3-phenylaminopropyl)piperazine, 1-[4,4-bis(4-fluorophenyl)butyl]-4-(2-hydroxy-3-phenylmethylaminopropyl)piperazine, 1-[4,4-bis-(4-fluorophenyl)butyl]-4-[3-(4-chlorophenylamino)-2-hydroxypropyl]piperazine, 1-[4,4-bis(4-fluorophenyl)butyl]-4-[3-(3,4-dichlorophenylamino)-2-hydroxypropyl]piperazine, 1-[4,4-bis(4-fluorophenyl)butyl]-4-[2-hydroxy-3-(2-methoxyphenylamino)propyl]piperazine, 1-[4,4-bis(4-fluorophenyl)butyl]-4-[3-(4-fluorophenylamino)-2-hydroxypropyl]piperazine, 1-[4,4-bis(4-fluorophenyl)butyl]-4-[2-hydroxy-3-(4-hydroxyphenylamino)propyl]piperazine, 1-[4,4-bis(4-fluorophenyl)butyl]-4-[2-hydroxy-3-(4-methoxyphenylamino)propyl]piperazine, 1-[4,4-bis(4-fluorophenyl)butyl]-4-[2-hydroxy-3-(3-methoxyphenylamino)propyl]piperazine, 1-[4,4-bis(4-fluorophenyl)butyl]-4-(2-acetoxy-3-phenylaminopropyl)piperazine, 1-(2,2-diphenylethyl)-4-(2-hydroxy-3-phenylaminopropyl)piperazine, 1-(3,3-diphenylpropyl)-4-(2-hydroxy-3-phenylaminopropyl)piperazine, 1-(4,4-diphenylbutyl)-4-(2-hydroxy-3-phenylaminopropyl)piperazine, 1-[bis(4-fluorophenyl)methyl]-4-(2-hydroxy-3-phenylaminopropyl)piperazine, 1-[bis(4-fluorophenyl)methyl]-4-[2-hydroxy-3-(4-methoxyphenylamino)propyl]piperazine, 1-[4,4-bis(4-fluorophenyl)butyl]-4-[2-hydroxy-3-(1-naphthylamino)propyl]piperazine, 1-[4,4-bis(4-fluorophenyl)butyl]-4-[2-hydroxy-3-(2,3,4-trimethoxyphenylamino)propyl]piperazine, 1-[4,4-bis(4-fluorophenyl)butyl]-4-[3-(3,4-dimethoxyphenylamino)-2-hydroxypropyl]piperazine, 1-[4,4-bis(4-fluorophenyl)butyl]-4-[3-hydroxy-3,5-di-tert-butylphenylamino)-2-hydroxypropyl]piperazine, 1-diphenylmethyl-4-(2-hydroxypropyl-3-phenylmethylamino)piperazine, 1-diphenylmethyl-4-[2-hydroxy-3-(2-phenylethylamino)propyl]piperazine, 1-diphenylmethyl-4-[2-hydroxy-3-{2-(2-methoxyphenyl)ethylamino}propyl]-piperazine, 1-[3-{2-(3,4-dimethoxyphenyl)ethylamino}-2-hydroxypropyl]-4-diphenylmethylpiperazine, 1-[4,4-bis(4-fluorophenyl)butyl]-4-[2-hydroxy-3-(2-phenylethylamino)-propyl]piperazine, 1-[4,4-bis(4-fluorophenyl)butyl]-4-[2-hydroxy-3-(4-nitrophenylamino)propyl]piperazine, 1-[4,4-bis(4-fluorophenyl)butyl]-4-[2-hydroxy-3-(3-phenylpropylamino)propyl]piperazine, 1-[4,4-bis(4-fluorophenyl)butyl]-4-[3-(4-chlorophenylmethylamino)-2-hydroxypropyl]piperazine, 1-[4,4-bis(4-fluorophenyl)butyl]-4-[3-(3,4-dichlorophenylmethylamino)-2- hydroxypropyl]piperazine, 1-[4,4-bis(4-fluorophenyl)-butyl]-4-[2-hydroxy-3-(4-methylphenylmethylamino)-propyl]piperazine, 1-[4,4-bis(4-fluorophenyl)butyl]-4-[2-hydroxy-3-(4-methoxyphenylmethylamino)propyl]-piperazine, 1-[4,4-bis(4-fluorophenyl)butyl]-4-[3-(2,3-dimethoxyphenylmethylamino)-2-hydroxypropyl]piperazine, 1-[4,4-bis(4-fluorophenyl)butyl]-4-[2-hydroxy-3-(2,3,4-trimethoxyphenylmethylamino)propyl]piperazine, 1-[4,4-bis(4-fluorophenyl)butyl]-4-[2-hydroxy-3-(N-methyl-N-phenylamino)propyl]piperazine, 1-[4,4-bis(4-fluorophenyl)butyl]-4-[2-hydroxy-3-(N-phenyl-N-phenylmethylamino)propyl]piperazine, 1-[3-(N-acetyl-N-phenylamino)-2-hydroxypropyl]-4-[4,4-bis(4-fluorophenyl)butyl]piperazine, 1-[4,4-bis(4-fluorophenyl)-butyl]-4-[3-(N-ethoxycarbonyl-N-phenylamino)-2-hydroxypropyl]piperazine, 1-[4,4-bis(4-fluorophenyl)-butyl]-4-[3-(N,N-diphenylamino)-2-hydroxypropyl]piperazine, 1-[4,4-bis(4-fluorophenyl)butyl]-4-[2-hydroxy-3-(N-methylsulfonyl-N-phenylamino)propyl]piperazine, 1-[4,4-bis(4-fluorophenyl)butyl]-4-[2-hydroxy-3-{N-(4-methylphenyl)sulfonyl-N-phenylamino }propyl]-piperazine, 1-4,4-bis(4-fluorophenyl)butyl]-4-(2-ethoxycarbonylmethoxy-3phenylthiopropyl)piperazine, and sodium 1-phenylthiomethyl-2-[4-{4,4-bis(4-fluorophenyl)butyl}piperazinyl]ethoxyacetate.

Such compounds represented by the general formula (1) or their salts according to the present invention can be, for instance, prepared in a conventional method in accordance with the following reaction scheme:

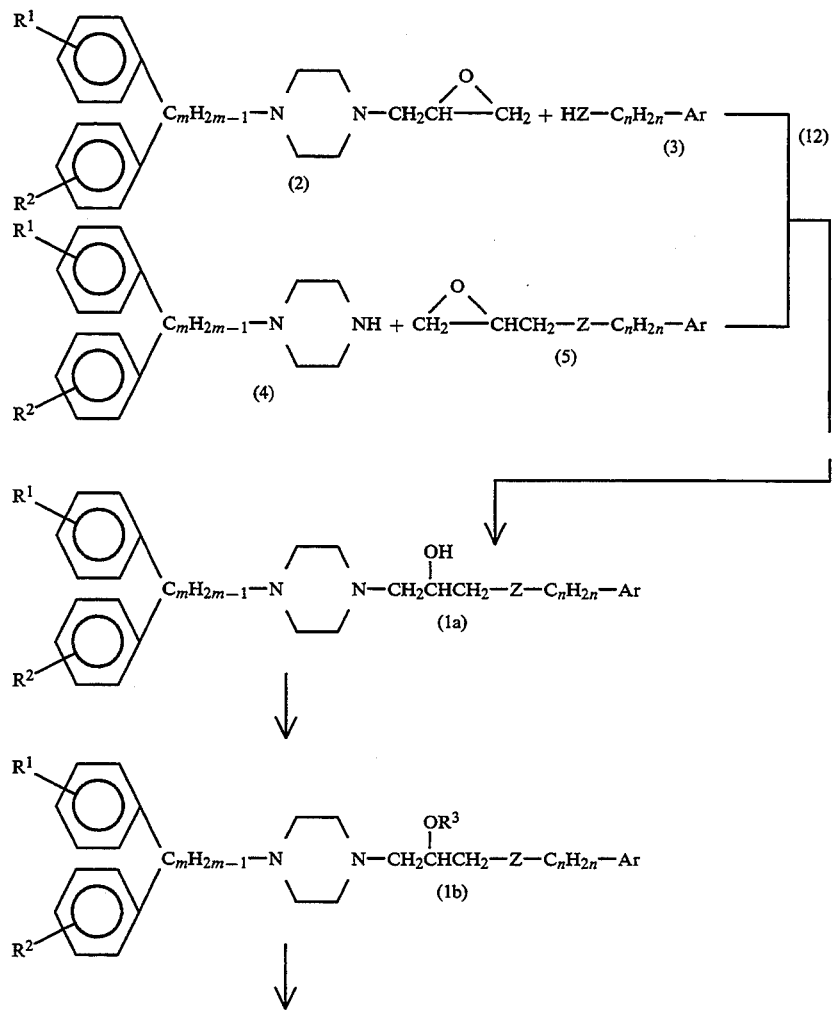

In this scheme, $R^1$, $R^2$, $R^3$, Z, m and n are the same as already referred to.

That is, a compound (2) and a compound (3) are reacted with each other in the presence or absence of an alkali catalyst in a solvent at room temperature or with heating, or a compound (4) and a compound (5) are reacted with each other in a solvent at room temperature or with heating to obtain the present compound (1a) wherein $R^3$ is a hydrogen atom. The obtained compound (1a) is then reacted with an alkylating agent, an aralkylating agent, an acylating agent or a nitrating agent to obtain a compound (1b) of the present invention wherein $R^3$ is an alkyl group, an aralkyl group, an acyl group or a nitro group.

Examples of the alkali catalyst useful in the reaction between the compounds (2) and (3) include potassium carbonate and sodium carbonate.

Examples of the solvent useful in the reaction between the compounds (2) and (3) or the compounds (4) and (5) include lower alcohols and dimethylformamide (hereinafter referred to as "DMF").

Examples of the reagent to be reacted with the compound (1a) include a combination of an alkyl halide or an aralkyl halide and a strong acid; acyl halides; acid anhydride—pyridine; and an acetic anhydride—concentrated nitric acid mixture.

Further, when an esterified carboxyl group or an esterified carboxymethyl group is present as a substituent in the compound (1), the elimination of the ester residue can be achieved by hydrolyzing the compound (1) according to a conventional method. To convert the obtained compound (1) of the present invention into a salt, conventional methods for preparing an acid addition salt of amine compounds or for preparing quaternary ammonium salts can be applied. For example, to prepare an acid addition salt, an acid is added to an organic solvent solution of the compound (1).

The crude product of the compound (1) of the present invention or its salts is refined by recrystallization, thin-layer chromatography, column chromatography, flush chromatography, fractional high pressure liquid chromatography or the like to obtain a pure compound (1) or its salts.

The thus obtained compound (1) of the present invention possesses an excellent antagonism against calcium and high safety and hence is useful for the prevention and cure of a variety of diseases as a drug for circulatory organs.

The drugs for circulatory organs of the present invention contain compound (1) of the present invention singly or as a mixture of two or more as an active ingredient or ingredients. These drugs are mixed with liquid or solid auxiliary components, which include an excipient, a binder and a diluent, so that drugs in the form of powder, granule, tablets, capsules, solution, injection or any other physical forms can be prepared and dosed orally or non-orally.

Although the dosing amount of the drug is suitably increased or decreased depending on the age, weight and the condition of the patient, the oral dose for an adult is preferably 10 to 1000 mg a day in terms of the compound (1), which may be divided into several times. Further, the drug can be mixed with other medicaments or agents when dosing the same, if necessary.

EXAMPLES:

The present invention will now be described in detail with reference to the exemplary embodiments, and it should be understood that these embodiments are given only for illustration of the invention and are not intended to be limitative therefor.

Example 1:

1-Diphenylmethyl-4- (2-hydroxy-3-phenylamino-propyl)-piperazine (compound 1 ):

3.08 g (0.01 mol) of 1-(diphenylmethyl)-4-(2,3-epoxypropyl)piperazine and 0.93 g (0.01 mol) of aniline were refluxed with heating together with 200 ml of DMF for 21 hours in the presence of a catalytic amount of an alkali such as potassium carbonate. DMF was distilled off under reduced pressure, and a residue was extracted with ethyl acetate. After washing with water and drying, the ethyl acetate was distilled off under reduced pressure to obtain 4 g of a crude subject compound of a viscous liquid. The obtained compound was refined by flush chromatography and fractional thin-layer chromatography by using solvent mixtures of ethyl acetate—methanol and methylene chloride—methanol respectively to obtain 2 g of the subject compound as yellow crystals.

$^1$H-NMR spectrum ($\delta$ ppm): 2.3–2.7 (m, 10H), 3.0–3.1 (m, 1H), 3.2–3.3 (m, 1H), 3.9–4.0 (m, 1H), 4.2 (s, 1H), 6.6–6.8 (m, 5H), 7.1–7.5 (m, 10H)

Mass spectrum: 402 (M+H)

IR spectrum: 3400, 2800, 1600, 1500, 1150 cm$^{-1}$ m.p. 158°–160° C.

Example 2:

1-Diphenylmethyl-4-(2-hydoxy-3-phenylmethylamino-propyl)piperazine (compound 2):

3.08 g (0.01 mol) of 1-(diphenylmethyl)-4-(2,3-epoxypropyl)piperazine and 1 g (0.01 mol) of benzylamine were refluxed with heating together with 200 ml of DMF for 5 hours in the presence of a catalytic amount of an alkali such as potassium carbonate. DMF was distilled off under reduced pressure, and a residue was extracted with ethyl acetate. After washing with water and drying, the ethyl acetate was distilled off under reduced pressure to obtain 4.8 g of a crude subject compound of a viscous liquid. The obtained compound was refined by flush chromatography and fractional thin-layer chromatography by using solvent mixtures of ethyl acetate—methanol and methylene chloride—methanol respectively to obtain 1.2 g of the subject compound as white crystals.

$^1$H-NMR spectrum ($\delta$ ppm): 2.2–2.7 (m, 12H), 3.7–3.9 (m, 3H), 4.2 (s, 1H), 7.1–7.5 (m, 15H)

Mass spectrum: 416 (M+H)

IR spectrum: 3400, 2800, 1600, 1500, 1150 cm$^{31\ 1}$ m.p. 76°–80° C.

Example 3:

1-Diphenylmethyl-4-[2-hydroxy-3-(2-phenylethylamino)propyl]piperazine (compound 3):

3.08 g (0.01 mol) of 1-(diphenylmethyl)-4-(2,3-epoxypropyl)piperazine and 1.2 g (0.01 mol) of 2-phenylethylamine were refluxed with heating together with 200 ml of DMF for 24 hours in the presence of a catalytic amount of an alkali such as potassium carbonate. DMF was distilled off under reduced pressure, and a residue was extracted with ethyl acetate. After washing with water and drying, the ethyl acetate was distilled off under reduced pressure to obtain 5 g of a crude subject compound of a viscous liquid. The obtained compound was refined by flush chromatography and fractional thin-layer chromatography by using solvent mixtures of ethyl acetate—methanol and methylene chloride—methanol respectively to obtain 1.5 g of the subject compound as white crystals.

$^1$H-NMR spectrum ($\delta$ ppm): 2.2–2.9 (m, 16H), 3.7–3.85 (m, 1H), 4.2 (s, 1H), 7.1–7.45 (m, 15H)

Mass spectrum: 430 (M+H)

IR spectrum: 3400, 2800, 1600, 1500, 1150 cm$^{-1}$ m.p. 114 –115° C.

Example 4:

1-Diphenylmethyl-4-[2-hydroxy-3-{2-(2-methoxyphenyl)ethylamino}propyl]piperazine (compound 4):

3.08 g (0.01 mol) of 1-(diphenylmethyl)-4-(2,3-epoxypropyl)piperazine and 2 g (0.01 mol) of 2-(2-methoxyphenyl)ethylamine were refluxed with heating together with 200 ml of DMF for 21 hours in the presence of a catalytic amount of an alkali such as potassium carbonate. DMF was distilled off under reduced pressure, and a residue was extracted with ethyl acetate. After washing with water and drying, the ethyl acetate was distilled off under reduced pressure to obtain 5.1 g of a crude subject compound of a viscous liquid. The obtained compound was refined by flush chromatography and fractional thin-layer chromatography with solvent mixtures of ethyl acetate—methanol and methylene chloride—methanol respectively to obtain 3.05 g of the subject compound in a viscous liquid state.

$^1$H-NMR spectrum ($\delta$): 2.2–2.9 (m, 16H), 3.8–3.9 (m, 4H), 4.2 (s, 1H), 6.75–6.85 (m, 2H), 7.1–7.4 (m, 12H)

Mass spectrum: 460 (M+H)

IR spectrum: 3400, 2800, 1600, 1500, 1150 cm$^{-1}$

Example 5:

1-[3-{2-(3,4-Dimethoxyphenyl)ethylamino}-2-hydroxypropyl]-4-diphenylmethylpiperazine (compound 5):

3.08 g (0.01 mol) of 1-(diphenylmethyl)-4-(2,3-epoxypropyl)piperazine and 2 g (0.01 mol) of 2-(3,4-dimethoxyphenyl)ethylamine were refluxed with heating together with 200 ml of DMF for 24 hours in the presence of a catalytic amount of an alkali such as potassium carbonate. DMF was distilled off under reduced pressure, and a residue was extracted with ethyl acetate, and after washing with water and drying, the ethyl acetate was distilled off under reduced pressure to obtain 5.1 g of a crude subject compound of a viscous liquid. The obtained compound was refined by flush chromatography and fractional thin-layer chromatography with solvent mixtures of ethyl acetate—methanol and methylene chloride—methanol respectively to obtain 1.2 g of the subject compound in a viscous liquid state.

$^1$H-NMR spectrum ($\delta$ ppm): 2.2–2.9 (m, 16H), 2.7–3.85 (m, 7H), 4.2 (s, 1H), 6.7–6.85 (m, 2H), 7.1–7.4 (m, 11H)

Mass spectrum: 90 (M+H)

IR spectrum: 400, 2800, 1600, 1500, 1150 cm$^{-1}$

Example 6:

1-[4,4-Bis(4-fluorophenyl)butyl]-4-(2-hydroxy-3-phenylaminopropyl)piperazine (compound 6):

3.86 g (0.01 mol) of 1-[4,4-bis(4-fluorophenyl)butyl]-4-(2,3-epoxypropyl)piperazine and 0.93 g (0.01 mol) of aniline were refluxed with heating with 200 ml of DMF for 21 hours in the presence of a catalytic amount of an alkali such as potassium carbonate. DMF was distilled off under reduced pressure, and a residue was extracted with ethyl acetate. After washing with water and drying, the ethyl acetate was distilled off under reduced pressure to obtain 5 g of a crude subject compound of a viscous liquid. The obtained compound was refined by flush chromatography and fractional thin-layer chromatography with solvent mixtures of ethyl acetate—methanol and methylene chloride —methanol respectively to obtain 0.5 g of the subject compound in a viscous liquid state.

$^1$H-NMR spectrum ($\delta$ ppm): 1.3–1.5 (m, 2H), 1.9–2.1 (m, 2H), 2.2–2.8 (m, 12H), 2.95–3.1 (m, 1H), 3.1–3.3 (m, 1H), 3.8–4 (m, 2H), 6.5–6.75 (m, 5H), 6.8–7.2 (m, 8H)

Mass spectrum: 480 (M+H)

IR spectrum: 3400, 2800, 1600, 1500, 1150 cm$^{-1}$

Example 7:

1-[4,4-Bis(4-fluorophenyl)butyl]-4-(2-hydroxy-3-phenylmethylaminopropyl)piperazine (compound 7):

3.86 g (0.01 mol) of 1-[4,4-bis(4-fluorophenyl)butyl]-4-(2,3-epoxypropyl)piperazine and 1 g (0.01 mol) of benzylamine were refluxed with heating together with 200 ml of DMF for 24 hours in the presence of a catalytic amount of an alkali such as potassium carbonate. DMF was distilled off under reduced pressure, and a residue was extracted with ethyl acetate. After washing with water and drying, the ethyl acetate was distilled off under reduced pressure to obtain 5 g of a crude subject compound of a viscous liquid. The obtained compound was refined by flush chromatography and fractional thin-layer chromatography with solvent mixtures of ethyl acetate—methanol and methylene chloride—methanol respectively to obtain 0.5 g of the subject compound in a viscous liquid state.

$^1$H-NMR spectrum ($\delta$ ppm): 1.3–1.5 (m, 2H), 1.9–2 (m, 2H), 2.1–2.7 (m, 12H), 3–3.15 (m, 2H), 3.75–3.9 (m, 2H), 4.55 (s, 2H), 6.8–7 (m, 5H), 7–7.4 (m, 8H)

Mass spectrum: 494 (M+H)

IR spectrum: 3400, 2800, 1600, 1500, 1150 cm$^{-1}$

Example 8:

1-[4,4-Bis(4-fluorophenyl)butyl]-4-[2-hydroxy-3-(2phenylethylamino)propyl]piperazine (compound 8):

3.86 g (0.01 mol) of 1-[4,4-bis(4-fluorophenyl)butyl]-4-(2,3-epoxypropyl)piperazine and 1.2 g (0.01 mol) of 2-phenylethylamine were refluxed with heating together with 200 ml of DMF for 24 hours in the presence of a catalytic amount of an alkali such as potassium carbonate. DMF was distilled off under reduced pressure, and a residue was extracted with ethyl acetate. After washing with water and drying, the ethyl acetate was distilled off under reduced pressure to obtain 5 g of a crude subject compound of a viscous liquid. The obtained compound was refined by flush chromatography and fractional thin-layer chromatography with solvent mixtures of ethyl acetate—methanol and methylene chloride—methanol respectively to obtain 0.5 g of the subject compound in a viscous liquid state.

$^1$H-NMR spectrum ($\delta$ ppm): 1.3–1.5 (m, 2H), 1.9–2.1 (m, 2H), 2.2–3 (m, 12H), 3–3.2 (m, 2H), 3.5–3.8 (m, 4H), 3.8–3.95 (m, 2H), 6.8–7 (m, 5H), 7–7.3 (m, 8H)

Mass spectrum: 508 (M+H)

IR spectrum: 3400, 2800, 1600, 1500, 1150 cm$^{-1}$

Example 9:

1-[4,4-Bis(4-fluorophenyl)butyl]-4-(2-hydroxy-3-phenylthiopropyl)piperazine (compound 9):

5.12 g (13.3 mmol) of 1-[4,4-bis(4-fluorophenyl)butyl]-4-(2,3-epoxypropyl)piperazine was dissolved in 100 ml of ethanol, and 6.0 g (54.5 mmol) of thiophenol was added to the mixture. The mixture was stirred for 5 hours at room temperature. The reaction mixture was poured into 100 ml of aqueous 10% sodium hydroxide solution, and after extracting with diethyl ether, the mixture was dried over anhydrous sodium sulfate. Under reduced pressure, the solvent was removed from the mixture by distillation to obtain 5.61 g of the subject compound as an oily material (yield: 89%).

NMR (CDCl$_3$, $\delta$ ppm):
1.3–1.5 (m, 2H), 1.9–2.1 (m, 2H),
2.2–2.7 (m, 12H), 2.9–3.1 (m, 2H),
3.7–3.9 (m, 2H), 6.9–7.4 (m, 13H)

Example 10:

1-[4,4-Bis(4-fluorophenyl)butyl]-4-(2-hydroxy-3-phenylthiopropyl)piperazine.2HCl (compound 10):

5.61 g (11.6 mmol) of the crude substance obtained in Example 9 was dissolved in 15 ml of ethanol, and 7.5 ml of 4.6N hydrochloric acid—ethanol solution was added to the mixture. The mixture was stirred for 15 minutes at room temperaure. After filtering out the insoluble matter, the mixture was washed twice with diethyl ether and was recrystallized from ethanol to obtain 5.21 g of the subject compound as white crystals (yield: 81%).

m.p. 174° to 176° C.

IR (KBr tablet):
3240, 2624–2348, 1603, 1508, 1439, 1222, 1159, 839, 760 cm$^{-1}$ NMR (DMSO-d$_6$, δ ppm):
1.40–1.60 (m, 2H), 1.99 (q, 2H, J=8 Hz),
2.90–3.90 (m, 14H), 3.95 (t, 1H, J=8 Hz),
4.12 (m, 1H), 7.00–7.17 (m, 5H),
7.17–7.40 (m, 8H)

Example 11:

1-[4,4-Bis(4-fluorophenyl)butyl]-4-(2-methoxy-3-phenylthiopropyl)piperazine (compound 11):

360 mg (0.7 mmol) of 1-[4,4-bis(4-fluorophenyl)-butyl]-4-(2-hydroxy-3-phenylthiopropyl) piperazine was dissolved in 5 ml of dried tetrahydrofuran, and 50 ml (1.1 mmol) of sodium hydride (purity of 5.5%) was added to the mixture. The mixture was stirred for 30 minutes at room temperature. 0.12 g (0.8 mmol) of methyl iodide was added to the mixture dropwise over approximately 45 minutes, and then the mixture was stirred overnight at room temperature. The reaction mixture was poured into 10 ml of distilled water, and after extracting with diethyl ether, the mixture was dried over anhydrous sodium sulfate. After removing the solvent from the mixture under reduced pressure, the residue was separated by column chromatography (silica gel, CHCl$_3$→CHCl$_3$: MeOH=100:3). The separated oily substance was dissolved in 10 ml of ethyl ether, and after washing with a saturated aqueous sodium carbonate solution, the mixture was dried over 35 anhydrous sodium sulfate. Under reduced pressure, the solvent was removed from the mixture by distillation to obtain 140 mg of the subject compound as an oily material (yield: 38%).

NMR (CDCl$_3$, δ ppm):
1.4–1.5 (m, 2H), 1.9–2.0 (m, 2H),
2.3–2.5 (m, 12H),
3.10 (d. d, 2H, J=7.3 Hz, J=17.3 Hz),
3.18 (s, 3H), 3.46 (t, t, 1H, J=7.3 Hz, J=7.8 Hz),
6.9–7.0 (m, 4H), 7.1–7.2 (m, 4H),
7.2–7.3 (m, 3H), 7.3–7.4 (m, 2H)

Example 12:

1-[4,4-Bis(4-fluorophenyl)butyl]-4-(2-methoxy-3-phenylthiopropyl)piperazine.2HCl (compound 12):

110 mg of the crude substance of the compound 11 obtained in Example 11 was dissolved in 2 ml of ether, and 1.0 ml of 4.6N hydrochloric acid—ethanol solution was added to the mixture. The mixture was stirred for 30 minutes at room temperature. After filtering out the insoluble matter, the mixture was washed twice with diethyl ether.

The obtained crude substance was recrystallized (ethanol—diethyl ether, 1:3) to obtain 80 mg of the subject compound as white crystals (yield: 63%).

IR (KBr tablet):
3240, 2950, 2440, 1480, 1420, 1220, 1090, 830 cm$^{-1}$

NMR (DMSO-d$_6$, δ ppm):
1.5–1.6 (m, 2H), 2.0–2.1 (m, 2H),
3.1–3.8 (m, 14H), 3.30 (s, 3H), 3.9–4.0 (m, 1H),
4.01 (t, 1H, J=7.8 Hz), 7.1–7.2 (m, 4H),
7.2–7.4 (m, 9H)

Example 13:

1-(2-Acetoxy-3-phenylthiopropyl)-4-[4,4-bis(4-fluorophenyl)butyl]piperazine (compound 13):

0.49 g (1.0 mmol) of 1-[4,4-bis(4-fluorophenyl)butyl]-4-(2-hydroxy-3-phenylthiopropyl) piperazine was dissolved in 2 ml of pyridine, and 500 mg (5.0 mmol) of acetic anhydride was added to the mixture. The mixture was stirred for 3.5 hours at room temperature. The reaction mixture was poured into 15 ml of distilled water, and after extracting with diethyl ether, the mixture was dried over anhydrous sodium sulfate. After removing the solvent from the mixture under reduced pressure, the residue was separated by the column chromatography (silica gel, CHCl$_3$→CHCl$_3$: MeOH=100:3). The separated oily substance was dissolved in 10 ml of diethyl ether, and after washing with a saturated aqueous sodium carbonate solution, the mixture was dried over the anhydrous sodium sulfate. Under reduced pressure, the solvent was removed from the mixture by distillation to obtain 410 mg of the subject compound as an oily material (yield: 77%).

NMR (CDCl$_3$, δ ppm):
1.3–1.4 (m, 2H), 1.9–2.0 (m, 2H), 1.93 (s, 3H),
2.2–2.3 (m, 10H), 2.52 (d, 2H, J=7.6 Hz),
3.21 (d. d, 2H, J=6.5 Hz, J=14.3 Hz),
3.85 (t, 1H, J=7.3 Hz), 5.10 (m, 1H),
6.8–7.5 (m, 13H)

Example 14:

1-(2-Acetoxy-3-phenylthiopropyl)-4-[4,4-bis(4-fluorophenyl)butyl]piperazine.2HCl (compound 14):

410 mg (0.76 mmol) of the crude substance of the compound 13 obtained in Example 13 was dissolved in 8 ml of ether, and 1.5 ml of 4.6N hydrochloric acid—ethanol solution was added to the mixture. After the mixture was stirred for 30 minutes at room temperature, the insoluble matter was filtered out. The insoluble matter was recrystallized (from ethanol—diethyl ether, 3:100) to obtain 290 mg of the subject compound as white crystals (yield: 62%).

IR (KBr tablet):
3350, 3000, 2350, 1740, 1510, 1220, 1040, 830 cm$^{-1}$

NMR (DMSO-d$_6$, δ ppm):
1.6–1.7 (m, 2H), 1.99 (s, 3H), 2.1–2.2 (m, 2H),
3.2–3.6 (m, 14H), 4.10 (t, 1H, J=8.1 Hz),
5.2–5.3 (m, 1H), 7.1–7.5 (m, 13H)

Referential Example 1:

(S)-(−)-1-[4,4-bis(4-fluorophenyl)butyl]-4-(2,3-epoxypropyl)piperazine:

250 mg (1.1 mmol) of (2R)-glycidyl tosylate was dissolved in 3 ml of dried methylene chloride, and, while stirring at room temperature, 2 ml of dried methylene chloride solution of 330 mg (1 mmol) of 1-[4,4-bis(4-fluorophenyl)butyl]piperazine and 0.4 ml (2.9 mmol) of triethylamine were successively added to the mixture. After stirring the mixture for 94.5 hours at the same temperature, the reaction liquid was poured in 10 ml of methylene chloride and 10 ml of 1N sodium hydroxide solution. The methylene chloride layer was separated, and the water layer was extracted with methylene chloride (7 ml ×2). The entire methylene chloride layers were combined and washed with a saturated saline solution (10 ml). After drying over anhydrous sodium sulfate, the solvent was removed from the mixture by distillation. The residue was treated by column chromatography (chloroform, chloroform: methanol=100:1) of silica gel, and a fraction (chloroform: methanol=100:1 effluent) was collected and concentrated. The residue was dissolved in 10 ml of the methylene chloride and was washed with 5 ml of 1N sodium hydroxide solution and 5 ml of a saturated saline solution, and after drying over anhydrous sodium sulfate, the solvent was removed by the distillation to obtain 123 mg of the subject compound as oily material (yield: 31.9%).

IR (KBr tablet):
1604, 1508, 1225, 1160, 830 cm$^{-1}$
NMR (CDCl$_3$, δ ppm):
1.37–1.50 (m, 2H), 1.99 (q, 2H, J=8 Hz),
2.23–2.80 (m, 14H), 3.05–3.15 (m, 1H),
3.86 (t, 1H, J=8 Hz), 6.90–7.05 (m, 4H),
7.10–7.25 (m, 4H)
$[\alpha]_D^{24}$ −7.4° (C=1.20, CHCl$_3$)

Referential Example 2:

(R)-(+)-1-[4,4-Bis(4-fluorophenyl)butyl]-4-(2,3-epoxypropyl)piperazine:

By using (2S)-glycidyl tosylate, the subject compound was obtained as an oily material in the same manner as Referential Example 1.

IR (KBr tablet):
1604, 1508, 1223, 1159, 828 cm$^{-1}$
NMR (CDCl$_3$, δ ppm):
1.37–1.50 (m, 2H), 1.99 (q, 2H, J=8 Hz),
2.23–2.80 (m, 14H), 3.05–3.15 (m, 1H),
3.86 (t, 1H, J=8 Hz), 6.90–7.05 (m, 4H),
7.10–7.25 (m, 4H)
$[\alpha]_D^{26}$ +7.2° (C=1.28, CHCl$_3$)

Example 15:

(S)-(−)-1-[4,4-Bis(4-fluorophenyl)butyl]-4-(2-hydroxy-3-phenylthiopropyl)piperazine (compound 15) and its dihydrochloride (compound 16):

125 mg (0.32 mmol) of (S)-(−)-1-[4,4-bis(4-fluorophenyl)butyl]-4-(2,3-epoxypropyl) piperazine was dissolved in 2 ml of ethanol, and, while stirring at room temperature in argon gas atmosphere, 0.05 ml (0.49 mmol) of thiophenol was added to the mixture at one time. The mixture was stirred for 5 hours under the same conditions. Then, the reaction liquid was poured in 8 ml of ether and 6 ml of 1N sodium hydroxide solution. The ether layer was separated, and the water layer was extracted with ether (6 ml ×2). The entire ether layers were combined and washed with a saturated saline solution (10 ml). After drying over anhydrous sodium sulfate, the solvent was removed from the mixture by distillation. The residue was treated by column chromatography (chloroform, chloroform: methanol=100:1) on a silica gel column, and a fraction (chloroform: methanol=100:1 effluent) was collected and concentrated. The residue was dissolved in 10 ml of ether and was washed with 5 ml of 1N sodium hydroxide solution and 5 ml of a saturated saline solution, and after drying over anhydrous sodium sulfate, the solvent was removed by distillation to obtain 148 mg of the subject (compound 15) in an oily material (yield: 91.9).

NMR (CDCl$_3$, δ ppm):
1.33–1.48 (m, 2H), 1.98 (q, 2H, J=8 Hz),
2.20–2.54 (m, 10H), 2.54–2.70 (m, 2H),
2.93–3.10 (m, 2H), 3.78–3.90 (m, 2H),
6.88–7.02 (m, 4H), 7.05–7.22 (m, 5H),
7.22–7.33 (m, 2H), 7.33–7.42 (m, 2H)
$[\alpha]_D^{26}$ −24.0° (C=1.48, CHCl$_3$)

148 mg of the obtained compound was dissolved in 2 ml of ether, and, while stirring in an iced water, 0.1 ml of concentrated hydrochloric acid was added to the mixture. After stirring for a while, white precipitation was filtered, dried and recrystallized from a solvent mixture of ethanol—ether (3:1) to obtain 96 mg of the dihydrochloride (compound 16) in a 56.5% yield.

m.p. 174°–176° C.
IR (KBr tablet):
3350, 2626–2364, 1604, 1508, 1439, 1221, 1160, 838 cm$^{-1}$
NMR (DMSO-d$_6$, δ ppm):
1.40–1.60 (m, 2H), 1.99 (q, 2H, J=8 Hz),
2.90–3.90 (m, 14H), 3.95 (t, 1H, J=8 Hz),
4.12 (m, 1H), 7.00–7.17 (m, 5H), 7.17–7.40 (m, 8H)
$[\alpha]_D^{25}$ −22.3° (C=0.3, MeOH)

Example 16:

(R)-(+)-1-[4,4-Bis(4-fluorophenyl)butyl]-4-(2-hydroxy-3-phenylthiopropyl)piperazine (compound 17) and its dihydrochloride (compound 18):

By using (R)-(+)-1-[4,4-bis(4-fluorophenyl)butyl]-4-(2,3-epoxypropyl)piperazine, the subject compounds were obtained in the same manner as Example 15.

Compound 17:
oily substance
NMR (CDCl$_3$, δ ppm):
1.35–1.50 (m, 2H), 1.99 (q, 2H, J=8 Hz),
2.20–2.55 (m, 10H), 2.55–2.70 (m, 2H),
2.94–3.13 (m, 2H), 3.80–3.92 (m, 2H),
6.90–7.02 (m, 4H), 7.10–7.24 (m, 5H),
7.24–7.35 (m, 2H), 7.35–7.43 (m, 2H)
$[\alpha]_D^{26}$ +21.20° (C=1.40, CHCl$_3$)

Compound 18:
white crystals
m.p. 174°–176° C.
IR (KBr tablet):
3350, 2626–2364, 1603, 1507, 1439, 1220, 1160, 837 cm$^{-1}$
NMR (DMSO-d$_6$, δ ppm):
1.40–1.60 (m, 2H), 1.99 (q, 2H, J=8 Hz),
2.90–3.90 (m, 14H), 3.95 (t, 1H, J=8 Hz),
4.12 (m, 1H), 7.00–7.17 (m, 5H), 7.17–7.40 (m, 8H)
$[\alpha]_D^{27.5}$ +20.4° (C=0.3, MeOH)

Example 17:

According to the methods described in Examples 9 and 10, the following compounds were obtained.

(1) 1-[4,4-Bis(4-fluorophenyl)butyl]-4-[2-hydroxy-3-(4methylphenylthio)propyl]piperazine (compound 19):
oily substance
NMR (CDCl$_3$, δ ppm):
1.32–1.48 (m, 2H), 1.98 (q, 2H, J=8 Hz),
2.20–2.52 (m, 10H), 2.31 (s, 3H),
2.52–2.68 (m, 2H), 2.87–3.06 (m, 2H),
3.74–3.90 (m, 2H), 6.89–7.00 (m, 4H),
7.03–7.19 (m, 6H), 7.23–7.33 (m, 2H)

(2) Dihydrochloride of compound 19 (compound 20):
white crystals
m.p. 170°–173° C.
IR (KBr tablet):
3350, 2626–2375, 1603, 1507, 1450, 1220, 1158, 838 cm$^{-1}$
NMR (DMSO-d$_6$, δ ppm):
1.55–1.75 (m, 2H), 2.14 (q, 2H, J=7.5 Hz),
2.35 (s, 3H), 3.00–4.00 (m, 14H),
4.10 (t, 1H, J=7.5 Hz), 4.22 (m, 1H),
7.10–7.27 (m, 6H), 7.27–7.50 (m, 6H)

(3) 1-[(4-Aminophenylthio)-2-hydroxypropyl]-4-[4,4bis(4-fluorophenyl)butyl]piperazine (compound 21):

oily substance
NMR (CDCl$_3$, δ ppm):
1.33–1.50 (m, 2H), 1.98 (q, 2H, J=8 Hz),
2.20–2.52 (m, 10H), 2.52–2.68 (m, 2H),
2.76–2.95 (m, 2H), 3.30–3.82 (m, 3H),
3.85 (t, 1H, J=8 Hz), 6.55–6.65 (m, 2H),
6.90–7.03 (m, 4H), 7.10–7.22 (m, 4H),
7.22–7.32 (m, 2H)

(4) Trihydrochloride of compound 21 (compound 22):
white crystals
m.p. 203°–206° C.
IR (KBr tablet):
3400, 2661–2375, 1602, 1507, 1493, 1450, 1413, 1219, 1159, 840, 820 cm$^{-1}$
NMR (DMSO-d$_6$, δ ppm):
1.57–1.77 (m, 2H), 2.14 (q, 2H, J=8 Hz),
2.90–4.05 (m, 16H), 4.10 (t, 1H, J=8 Hz),
4.26 (m, 1H), 7.19 (t, 4H, J=9 Hz),
7.34 (d, 2H, J=8.5 Hz), 7.38–7.50 (m, 4H),
7.56 (d, 2H, J=8.5 Hz)

(5) 1-[Bis(4-fluorophenyl)methyl ]-4-(2-hydroxy-3-phenylmethylthiopropyl)piperazine (compound 23):
oily substance
NMR (CDCl$_3$, δ ppm):
2.20–2.47 (m, 8H), 2.50 (d, 2H, J=6 Hz),
2.53–2.70 (m, 2H), 3.68–3.83 (m, 1H),
3.76 (s, 2H), 4.20 (s, 1H), 6.88–7.00 (m, 4H),
7.17–7.40 (m, 9H)

(6) Dihydrochloride of compound 23 (compound 24):
white crystals
m.p. 159°–162° C.
IR (KBr tablet):
3395, 3362, 2633–2345, 1606, 1513, 1435, 1233, 1166, 861, 835 cm$^{-1}$
NMR (DMSO-d$_6$, δ ppm):
2.80–3.75 (m, 10H), 3.80 (s, 2H),
4.00–4.60 (m, 4H), 7.10–7.40 (m, 9H),
7.65–7.95 (m, 4H), (7) 1-[3,3-Bis(4-fluorophenyl)propyl]-4-(2-hydroxy-3-phenylthiopropyl)piperazine (compound 25):
oily substance
NMR (CDCl$_3$, δ ppm):
2.10–2.28 (m, 4H), 2.28–2.55 (m, 8H),
2.55–2.80 (m, 2H), 2.93–3.12 (m, 2H),
3.79–3.91 (m, 1H), 3.96 (t, 1H, J=7 Hz),
6.90–7.02 (m, 4H), 7.10–7.22 (m, 5H),
7.22–7.32 (m, 2H), 7.32–7.42 (m, 2H), (8) Dihydrochloride of compound 25 (compound 26):
white crystals
m.p. 192°–195° C.
(KBr tablet):
3282, 2622–2402, 1603, 1580, 1509, 1439, 1231, 1160, 827, 738 cm$^{-1}$
NMR (DMSO-d$_6$, δ ppm):
2.80–4.12 (m, 16H), 4.12–4.35 (m, 2H),
7.10–7.33 (m, 5H), 7.33–7.57 (m, 8H), (9) 1-[4,4-Bis(4-fluorophenyl)butyl]-4-(2-hydroxy-3-phenylmethylthiopropyl)piperazine (compound 27):
oily substance
NMR (CDCl$_3$, δ ppm):
1.35–1.47 (m, 2H), 1.94–2.03 (q, 2H),
2.26–2.59 (m, 14H), 3.71–3.89 (m, 4H),
6.91–7.00 (t. t, 4H), 7.12–7.34 (m, 9H)

(10) Dihydrochloride of compound 27 (compound 28):
white crystals
m.p. 145°–148° C.
IR(KBr tablet):
3400, 3000, 2600, 2500, 1500, 1200, cm$^{-1}$
NMR (CDCl$_3$, δ ppm):
1.70–2.85 (m, 2H), 2.08–2.16 (q, 2H),
3.10–3.42 (m, 4H), 3.60–3.80 (m, 10H),
3.96 (t, 1H, J=8 Hz), 4.10–4.22 (m, 1H),
6.99 (t, 4H, J=8.9 Hz), 7.20–7.37 (m, 9H)

(11) 1-Diphenylmethyl-4-(2-hydroxy-3-phenylthiopropyl)piperazine (compound 29):
white crystals
m.p. 119°–121° C.
IR (KBr tablet):
3800, 2800, 1600, 1500, 1180, 1100 cm$^{-1}$
NMR (CDCl$_3$, δ ppm):
2.30–2.70 (m, 10H), 2.90–3.20 (m, 2H),
3.30–3.70 (bs, 1H), 3.80–3.90 (m, 1H),
4.2 (s, 1H), 7.10–7.50 (m, 15H)

(12) 1-[4,4-Bis(4-fluorophenyl)butyl]-4-[3-(4-chlorophenylthio)-2-hydroxyproply]piperazine (compound 30):
oily substance
NMR (CDCl$_3$, δ ppm):
1.3—1.5 (m, 2H), 1.9–2.1 (q, 2H),
2.2–2.5 (m, 10H), 2.5–2.7 (m, 2H) ,
2.9–3.1 (m, 2H), 3.8–3.9 (m, 2H) ,
6.9–7.4 (m, 12H)

(13) Dihydrochloride of compound 30 (compound 31):
white crystals
m.p. 163°–166 ° C.
IR (KBr tablet):
370, 2340, 1510, 1220, 1160, 840 cm$^{-1}$
NMR (DMSO-d$_6$, δ ppm):
1.5–1.8 (m, 2H), 2.0–2.3 (q, 2H),
3.0–4.0 (m, 14H), 4.10 (t, 1H, J=7.6 Hz),
4.2–4.3 (m, 1H), 7.1–7.3 (m, 4H),
7.4–7.6 (m, 8H)

(14) 1-[4,4-Bis(4-fluorophenyl)butyl]-4-[3-(3,4-dichlorophenylthio)-2-hydroxypropyl]piperazine (compound 32):
oily substance
NMR (CDCl$_3$, δ ppm):
1.4–1.5 (m, 2H), 1.9–2.1 (q, 2H),
2.2–2.6 (m, 12H), 2.6–2.8 (m, 2H),
3.01 (d, 2H, J=6.9 Hz), 3.8–3.9 (m, 2H),
6.9–7.5 (m, 11H)

(15) Dihydrochloride of compound 32 (compound 33):
white crystals
m.p. 157°–160° C.
IR (KBr tablet):
3340, 2330, 1510, 1460, 1230, 1160, 840 cm$^{-1}$
NMR (DMSO-d$_6$, δ ppm):
1.6–1.8 (m, 2H), 2.1–2.3 (q, 2H),
3.1–4.0 (m, 14H), 4.10 (t, 1H, J=7.6 Hz),
4.2–4.3 (m, 1H), 7.1–7.8 (m, 11H)

(16) 1-[4,4-Bis(4-fluorophenyl)butyl]-4-[2-hydroxy-3-(2-methoxyphenylthio)propyl]piperazine (compound 34):
oily substance
NMR (CDCl$_3$, δ ppm):
1.3–1.5 (m, 2H), 1.9–2.1 (q, 2H),
2.2–2.7 (m, 12H), 2.9–3.1 (m, 2H),
3.7–3.9 (m, 5H), 6.8–7.4 (m, 12H)

(17) Dihydrochloride of compound 34 (compound 35):
white crystals
m.p. 158°–161° C.

IR (KBr tablet):
3260, 2370, 1510, 1230, 1020, 830 cm$^{-1}$
NMR (DMSO-d$_6$, δ ppm):
1.6–1.8 (m, 2H), 2.1–2.2 (q, 2H),
3.0–3.8 (m, 14H), 3.91 (s, 3H),
4.10 (t, 1H, J=7.8 Hz), 4.2–4.3 (m, 1H),
7.0–7.5 (m, 12H)

(18) 1-[4,4-Bis(4-fluorophenyl)butyl]-4-[3-(4-fluorophenylthio)-2-hydroxypropyl]piperazine (compound 36):
oily substance
NMR (CDCl$_3$, δ ppm):
1.41 (t. t, 2H, J=7.8 Hz, J=8.1 Hz),
1.98 (d. t, 2H, J=7.8 Hz, J=7.8 Hz),
2.3–2.5 (m, 10H), 2.4–2.6 (m, 2H),
2.9–3.0 (m, 2H), 3.7–3.8 (m, 1H),
3.85 (t, 1H, J=7.8 Hz), 6.9–7.0 (m, 6H),
7.1–7.2 (m, 4H), 7.3–7.4 (m, 2H)

(19) Dihydrochloride of compound 36 (compound 37):
white crystals
m.p. 180°–182° C.
IR (KBr tablet):
3340, 2390, 1500, 1450, 1230, 1160, 830 cm$^{-1}$
NMR (DMSO-d$_6$, δ ppm):
1.6–1.7 (m, 2H), 2.1–2.2 (m, 2H),
3.2–4.0 (m, 14H), 4.27 (t, 1H, J=5.9 Hz),
4.2–4.3 (m, 1H), 7.1–7.6 (m, 12H)

(20) 1-[4,4-Bis(4-fluorophenyl)butyl]-4-[2-hydroxy-3-(4-hydroxyphenylthio)propyl]piperazine (compound 38):
oily substance
NMR (CDCl$_3$, δ ppm):
1.4–1.5 (m, 2H), 2.0–2.1 (m, 2H),
2.3–2.5 (m, 10H), 2.7–2.8 (m, 2H),
2.9–3.0 (m, 2H), 3.8 (t, 1H, J=7.8 Hz),
3.8–3.9 (m, 1H), 4.9–5.0 (br, 2H),
6.65 (d, 2H, J=8.4 Hz), 6.9–7.1 (m, 4H),
7.1–7.2 (m, 4H), 7.40 (d, 2H, J=8.4 Hz)

(21) Dihydrochloride of compound 38 (compound 39):
white crystals
m.p. 208°–210° C.
IR (KBr tablet):
3250, 2390, 1510, 1270, 1160, 840 cm$^{-1}$
NMR (DMSO-d$_6$, δ ppm):
1.6–1.7 (m, 2H), 2.1–2.2 (m, 2H),
3.1–4.0 (m, 14H), 4.0–4.2 (m, 2H),
6.8–6.9 (m, 2H), 7.1–7.2 (m, 4H),
7.4–7.5 (m, 6H)

(22) 1-[4,4-Bis(4-fluorophenyl)butyl]-4-[2-hydroxy-3-(4-methoxyphenylthio)propyl]piperazine (compound 40):
oily substance
NMR (CDCl$_3$, δ ppm):
1.3–1.5 (m, 2H), 1.9–2.0 (m, 2H),
2.4–2.6 (m, 12H), 2.89 (t, 2H, J=7.8 Hz),
3.76 (s, 3H), 3.8–3.9 (m, 2H),
6.80 (dd, 2H, J=2.4 Hz, J=4.9 Hz),
6.9–7.0 (m, 4H), 7.1–7.2 (m, 4H),
7.38 (dd, 2H, J=2.4 Hz, J=4.9 Hz)

(23) Dihydrochloride of compound 40 (compound 41):
white crystals
m.p. 182°–185° C.
IR (KBr tablet):
350, 2940, 2380, 1600, 1440, 1220, 830 cm$^{-1}$
NMR (DMSO-d$_6$, δ ppm):
1.4–1.6 (m, 2H), 2.0–2.2 (m, 2H),
2.3–2.7 (m, 12H), 2.9–3.0 (m, 2H),
3.83 (s, 3H), 3.9–4.0 (m, 2H), 6.8–7.2 (m, 12H)

(24) 1-[4,4-Bis(4-fluorophenyl)butyl]-4-[2-hydroxy-3-(3-methoxyphenylthio)propyl]piperazine (compound 42):
oily substance
NMR (CDCl$_3$, δ ppm):
1.4–1.5 (m, 2H), 1.9–2.0 (m, 2H),
2.3–2.5 (m, 10H), 2.6–2.7 (m, 2H),
2.9–3.0 (m, 2H), 3.76 (s, 3H), 3.8–3.9 (m, 2H),
6.6–6.7 (m, 1H), 6.9–7.0 (m, 6H),
7.1–7.2 (m, 5H)

(25) Dihydrochloride of compound 42 (compound 43):
white crystals
m.p. 175°–178° C.
IR (KBr tablet):
250, 2920, 2430, 1600, 1470, 1290, 1160, 1040, 840 cm$^{-1}$
NMR (DMSO-d$_6$, δ ppm):
1.5–1.7 (m, 2H), 2.0–2.2 (m, 2H),
2.3–2.8 (m, 12H), 3.0–3.2 (m, 2H),
3.80 (s, 3H), 3.9–4.0 (m, 2H), 6.9–7.0 (m,
7.1–7.3 (m, 4H), 7.4–7.5 (m, 3H)

(26) 1-[Bis(4-fluorophenyl)methyl]-4-[2-hydroxy-3-(2methoxyphenylthio)propyl]piperazine (compound 44):
oily substance
NMR (CDCl$_3$, δ ppm):
2.4–2.6 (m, 12H), 2.9–3.1 (m, 2H),
3.8–3.9 (m, 1H), 3.87 (s, 3H), 4.19 (s, 1H),
6.8–7.0 (m, 6H), 7.1–7.4 (m, 6H)

(27) Dihydrochloride of compound 44 (compound 45):
white crystals
m.p. 160°–163° C.
IR (KBr tablet):
3250, 2300, 1580, 1510, 1440, 1280, 840 cm$^{-1}$
NMR (DMSO-d$_6$, δ ppm):
3.1–3.3 (m, 4H), 3.5 3.7 (m, 9H), 3.65 (s, 3H),
4.15 (t, 1H, J=7.3 Hz), 8.90 (d, 2H, J=8.9 Hz),
7.2–7.3 (m, 4H), 7.42 (d, 2H, J=8.9 Hz),
7.8–8.0 (m, 4H),

(29) 1-(2,2-Diphenylethyl)-4-(2-hydroxy-3-phenylthiopropyl)piperazine (compound 46):
oily substance
NMR (CDCl$_3$, δ ppm):
2.3–2.6 (m, 10H), 2.9–3.1 (m, 4H),
3.7–3.9 (m, 1H), 4.18 (t, 1H, J=7.6 Hz),
7.1–7.4 (m, 15H)

(30) Dihydrochloride of compound 46 (compound 47):
white crystals
m.p. 163°–165° C.
IR (KBr tablet):
3430, 2360, 1450, 1090, 740 cm$^{-1}$
NMR (DMSO-d$_6$, δ ppm):
3.2–3.7 (m, 12H), 4.0–4.2 (m, 2H),
4.27 (t, 1H, J=6.8 Hz), 4.80 (brs, 1H),
7.2–7.6 (m, 15H)

(31) 1-(3,3-Diphenylpropyl)-4-(2-hydroxy-3-phenylthiopropyl)piperazine (compound 48):
oily substance
NMR (CDCl$_3$, δ ppm):
2.2–2.7 (m, 14H), 2.9–3.1 (m, 2H),
3.8–3.9 (m, 1H), 3.97 (t, 1H, J=6.8 Hz),
7.1–7.4 (m, 15H)

(32) Dihydrochloride of compound 48 (compound 49):
white crystals
m.p. 193°–196° C.
IR (KBr tablet):
3270, 2990, 2350, 1490, 1090, 740 cm$^{-1}$
NMR (DMSO-d$_6$, δ ppm):
2.5–2.7 (m, 2H), 3.1–3.9 (m, 16H),
4.14 (t, 1H, J=7.3 Hz), 4.2–4.3 (m, 1H),
7.2–7.5 (m, 15H)

(33) 1-(4,4-Diphenylbutyl)-4-(2-hydroxy-3-phenylthiopropyl)piperazine (compound 50):
oily substance
NMR (CDCl$_3$, δ ppm):
1.36 (t. t, 2H, J=7.6 Hz, J=7.8 Hz),
1.95 (d. t, 2H, J=7.8 Hz, J=7.8 Hz),
2.1–2.7 (m, 12H), 2.9–3.0 (m, 2H),
3.7–3.8 (m, 2H), 7.0–7.3 (m, 15H)

(34) Dihydrochloride of compound 50 (compound 51):
white crystals
m.p. 197°–199° C.
IR (KBr tablet):
3220, 2500, 1470, 1240, 1070, 760 cm$^{-1}$
NMR (DMSO-d$_6$, δ ppm):
1.6–1.7 (m, 2H), 2.1–2.2 (m, 2H),
3.2–3.9 (m, 14H), 4.05 (t, 1H, J=6.8 Hz),
4.2–4.3 (m, 1H), 7.2–7.5 (m, 15H)

(35) 1-[Bis(4-fluorophenyl)methyl]-4-(2-hydroxy-3-phenylthiopropyl)piperazine (compound 52):
oily substance
NMR (CDCl$_3$, δ ppm):
2.3–2.5 (m, 8H), 2.5–2.6 (m, 2H),
2.9–3.1 (m, 2H), 3.8–3.9 (m, 1H),
4.19 (s, 1H), 6.9–7.0 (m, 4H), 7.1–7.4 (m, 9H)

(36) Dihydrochloride of compound 52 (compound 53):
white crystals
m.p. 143°–146° C.
IR(KBr tablet):
3480, 2430, 1610, 1500, 1440, 1240, 830 cm$^{-1}$
NMR (DMSO-d$_6$, δ ppm):
2.7–3.2 (m, 4H), 3.4–3.7 (m, 9H),
4.16 (t, 1H, J=4.1 Hz), 7.2–7.4 (m, 10H),
7.6–7.7 (m, 3H)

(37) 1-[Bis (4-fluorophenyl)methyl]-4-[2-hydroxy-3-(4-methoxyphenylthio)propyl]piperazine (compound 54):
oily substance
NMR (CDCl$_3$, δ ppm):
2.4–2.6 (m, 10H), 2.9–3.0 (m, 2H),
3.6–3.7 (m, 1H), 3.69 (s, 3H), 4.2 (s, 1H),
6.8–7.0 (m, 6H), 7.3–7.4 (m, 6H)

(38) Dihydrochloride of compound 54 (compound 55):
white crystals
m.p. 162°–164° C.
IR (KBr tablet):
3260, 2300, 1610, 1490, 1440, 1280, 830 cm$^{-1}$
NMR (DMSO-d$_6$, δ ppm):
3.0–3.2 (m, 2H), 3.4–4.0 (m, 11H),
3.78 (s, 3H), 4.0–4.1 (m, 1H),
6.89 (d, 2H, J=8.9 Hz), 7.22 (t, 4H, J=8.4 Hz),
7.39 (d, 2H, J=8.9 Hz), 7.7–7.8 (m, 4H)

(39) 1-[4,4-Bis(4-fluorophenyl)butyl]-4-[2-hydroxy-3-(1-naphthylthio)propyl]piperazine (compound 56):
oily substance
NMR (CDCl$_3$, δ ppm):
1.2–1.4 (m, 2H), 2.0–2.1 (m, 2H),
2.3–2.6 (m, 18H), 3.0–3.1 (m, 2H),
3.84 (t, 1H, J=7.0 Hz), 6.9–7.0 (m, 4H),
7.1–7.2 (m, 4H), 7.4–7.9 (m, 6H),
8.43 (d, 1H, J=8.1 Hz)

(40) Dihydrochloride of compound 56 (compound 57):
white crystals
m.p. 180°–182° C.
IR (KBr tablet):
3300, 2240, 1510, 1470, 1200, 830 cm$^{-1}$
NMR (DMSO-d$_6$, δ ppm):
1.6–1.7 (m, 2H), 2.1–2.2 (m, 2H),
3.2–3.9 (m, 18H), 4.10 (t, 1H, J=7.3 Hz),
4.3–4.4 (m, 1H), 7.2–7.7 (m, 11H),
7.78 (d, 1H, J=7.6 Hz), 7.92 (d, 1H, J=7.6 Hz),
8.04 (d, 1H, J=7.6 Hz), 8.36 (d, 1H, J=7.6 Hz)

(41) 1-[4,4-Bis(4-fluorophenyl)butyl]-4-[2-hydroxy-3-(N-methyl-N-phenylamino)propyl]piperazine (compound 58):
oily substance
NMR (DMSO-d$_6$, δ ppm):
1.35–1.52 (m, 2H), 1.99 (q, 2H, J=8 Hz),
2.25–2.56 (m, 10H), 2.56–2.76 (m, 2H),
2.99 (s, 3H), 3.37 (d, 2H, J=9.5 Hz),
3.86 (t, 1H, J=8 Hz), 3.91–4.05 (m, 1H),
6.68–6.83 (m, 3H), 6.92–7.07 (m, 4H),
7.10–7.33 (m, 6H)

(42) Trihydrochloride of compound 58 (compound 59):
white crystals
m.p. 192°–195° C.
IR (KBr tablet):
3425, 3235 (shoulder), 2638–2450, 1603, 1509, 1222, 1158, 835 cm$^{-1}$
NMR (DMSO-d$_6$, δ ppm):
1.56–1.76 (m, 2H), 2.04–2.20 (m, 2H),
3.06 (s, 3H), 3.12–3.98 (m, 14H),
4.10 (t, 1H, J=8 Hz), 4.16–4.42 (m, 1H),
6.68 (t, 1H, J=7.3 Hz), 6.98 (d, 2H, J=7.3 Hz),
7.19 (t, 4H, J=8.6 Hz), 7.30 (t, 2H, J=7.7 Hz),
7.35–7.50 (m, 4H)

(43) 1-[4,4-Bis(4-fluorophenyl)butyl]-4-[3-(3,4-dimethoxyphenylthio)-2-hydroxypropyl]piperazine (compound 60):
oily substance
NMR (CDCl$_3$, δ ppm):
1.3–1.4 (m, 2H), 1.9–2.0 (m, 2H),
2.3–2.7 (m, 12H), 3.8–4.0 (m, 2H),
3.84 (s, 3H), 3.85 (s, 3H), 6.9–7.0 (m, 7H),
7.1–7.2 (m, 4H)

(44) Dihydrochloride of compound 60 (compound 61):
white crystals
m.p. 139°–141° C.
IR (KBr tablet):
3430, 2950, 2360, 1450, 1020, 830 cm$^{-1}$
NMR (DMSO-d$_6$, δ ppm):
1.5–1.6 (m, 2H), 2.0–2.1 (m, 2H),
3.1–3.7 (m, 14H), 3.74 (s, 3H), 3.77 (s, 3H),
4.0–4.1 (m, 1H), 4.01 (t, 1H, J=8 Hz),
6.9–7.1 (m, 6H), 7.3–7.4 (m, 5H)

(45) 1-[4,4-Bis(4-fluorophenyl)butyl]-4-[3-(4-chlorophenylmethylthio)-2-hydroxypropyl]piperazine(compound 62):
oily substance
NMR (CDCl$_3$, δ ppm):
1.4–1.5 (m, 2H), 2.0–2.1 (m, 2H), 2.3–2.5 (m, 12H), 2.6–2.7 (m, 2H),
3.7–3.8 (m, 3H), 3.86 (t, 1H, J=8.1 Hz),
6.9–7.0 (m, 4H), 7.1–7.2 (m, 4H),
7.2–7.3 (m, 4H)

(46) Dihydrochloride of compound 62 (compound 63):
white crystals
m.p. 136°–138° C.
IR (KBr tablet):
3320, 2550, 2340, 1450, 1160, 1090, 840 cm$^{-1}$
NMR (DMSO-d$_6$, δ ppm):
1.5–1.6 (m, 2H), 1.9–2.0 (m, 2H),
3.0–3.8 (m, 14H), 3.74 (s, 2H),
3.95 (t, 1H, J=8.1 Hz), 4.1–4.2 (m, 1H),
7.0–7.1 (m, 4H), 7.2–7.3 (m, 8H)

(47) 1-[4,4-Bis(4-fluorophenyl)butyl]-4-[2-hydroxy-3-(4-methoxyphenylmethylthio) propyl]piperazine (compound 64):
oily substance
NMR (CDCl$_3$, δ ppm):
1.5–1.6 (m, 2H), 2.0–2.1 (m, 2H),
2.4–2.7 (m, 14H), 3.81 (s, 2H), 3.84 (s, 3H),
3.8–3.9 (m, 1H), 3.96 (t, 1H, J=8.1 Hz),
6.9–7.0 (m, 2H), 7.0–7.1 (m, 4H),
7.2–7.3 (m, 4H), 7.4–7.5 (m, 2H)

(48) Dihydrochloride of compound 64 (compound 65):
white crystals
m.p. 162°–164° C.
IR (KBr tablet):
320, 2870, 2360, 1450, 1250, 840 cm$^{-1}$
NMR (DMSO-d$_6$, δ ppm):
1.5–1.6 (m, 2H), 2.0–2.1 (m, 2H),
3.1–3.8 (m, 14H), 3.72 (s, 3H), 3.75 (s, 2H),
4.04 (t, 1H, J=8.1 Hz), 4.1–4.2 (m, 1H),
6.89 (d, 2H, J=8.9 Hz), 7.1–7.2 (m, 4H),
7.26 (d, 2H, J=8.9 Hz), 7.3–7.4 (m, 4H)

(49) 1-[4,4-Bis(4-fluorophenyl)butyl]-4-[2-hydroxy-3-(3-phenylpropylthio)propyl]piperazine (compound 66):
oily substance
NMR (CDCl$_3$, δ ppm):
1.4–1.5 (m, 2H), 1.9–2.1 (m, 4H),
2.3–2.7 (m, 18H), 3.7–3.8 (m, 1H),
3.85 (t, 1H, J=8.1 Hz), 6.9–7.0 (m, 3H),
7.2–7.3 (m, 10H)

(50) Dihydrochloride of compound 66 (compound 67):
white crystals
m.p. 183°–186° C.
IR (KBr tablet):
3430, 2340, 1650, 1510, 1160 cm$^{-1}$
NMR (DMSO-d$_6$, δ ppm):
1.6–1.7 (m, 2H), 1.92 (Sep, 2H, J=7.6 Hz),
2.1–2.2 (m, 2H), 2.6–2.8 (m, 8H),
3.1–3.8 (m, 10H), 4.10 (t, 1H, J=7.6 Hz),
4.2–4.3 (m, 1H), 7.2–7.5 (m, 13H)

(51) 1-[4,4-Bis(4-fluorophenyl)butyl]-4-[2-hydroxy-3-(4-nitrophenylthio)propyl]piperazine (compound 68):
oily substance
NMR (CDCl$_3$, δ ppm):
1.3–1.5 (m, 2H), 1.9–2.1 (q, 2H),
2.2–2.7 (m, 12H), 3.1–3.2 (d, 2H),
3.86 (t, 1H, J=7.7 Hz), 3.9–4.0 (m, 1H),
6.9–7.0 (m, 4H), 7.1–7.2 (m, 4H),
7.4–7.5 (m, 2H), 8.1–8.2 (m, 2H)

(52) Dihydrochloride of compound 68 (compound 69):
light yellow crystals
m.p. 184°–187° C.
IR (KBr tablet):
3420, 2360, 1510, 1340, 1220, 1090, 840 cm$^{-1}$
NMR (DMSO-d$_6$, δ ppm):
1.6–1.8 (m, 2H), 2.1–2.3 (q, 2H),
3.1–3.9 (m, 14H), 4.10 (t, 1H, J=8.1 Hz),
4.2–4.4 (m, 1H), 7.1–7.3 (m, 4H),
7.3–7.5 (m, 4H), 7.6–7.7 (m, 2H),
8.2–8.3 (m, 2H)

Referential Example 3:

Synthesis of N-(2,3-epoxypropyl)-N-methylsulfonylaniline:

1.7 g (0.01 mol) of N-methylsulfonylaniline was dissolved in 100 ml of methylene chloride, and 7 g (0.051 mol) of epibromohydrin was added to the mixture. To this mixture, a solution obtained by adding 12 g (0.047 mol) of tetrabutylammonium bromide and 2 g (0.05 mol) of sodium hydroxide into 5 ml of water, was gradually added. The mixture was stirred overnight. After washing three times with 50 ml of water, the methylene chloride was distilled off under reduced pressure. The obtained residue was refined by the silica gel chromatography to obtain 1.9 g of the subject compound as a light-yellowish oily material (yield: 83.7).

IR (KBr tablet):
1595, 1499, 1337, 1160 cm$^{-1}$
NMR (CDCl$_3$, δ ppm):
7.27–7.47 (m, 5H), 3.72–4.13 (m, 2H),
3.15–3.21 (m, 1H), 2.97 (s, 3H),
2.76–2.80 (dd, 1H), 2.52–2.54 (dd, 1H)

Example 18:

1-[4,4-Bis(4-fluorophenyl)butyl]-4-[2-hydoxy-3-(N-methylsulfonyl-N-phenylamino)propyl]piperazine (compound 70) and its dihydrochloride (compound 71):

1.9 g (0.083 mol) of N-(2,3-epoxypropyl)-N-methylsulfonylaniline and 3.3 g (0.01 mol) of 1-[4,4-bis(4-fluorophenyl)butyl]piperazine were dissolved in 100 ml of ethanol, and the mixture was stirred overnight at a room temperature. After distilling off the solvent from the reaction mixture under reduced pressure, the residue was refined by silica gel chromatography to obtain 2.8 g of a subject compound (compound 70) as a light-yellowish oily material (yield: 62%).

1 g of the obtained compound was dissolved in absolute ethanol, and 2 ml of concentrated hydrochloric acid was added dropwise to the mixture. The solvent was distilled off from the mixture under reduced pressure to obtain 1.12 g of the subject dihydrochloride (compound 71) as a white amorphous (yield: 98.6).

Compound 70:
NMR (CDCl$_3$, δ ppm):
7.65–7.31 (m, 5H), 7.17–7.11 (m, 4H),
7.02–6.87 (m, 4H), 3.88–3.70 (m, 3H),
3.65–3.48 (m, 1H), 3.01 (s, 3H),
2.47–2.27 (m, 12H), 2.09–1.93 (2H),
1.52–1.23 (m, 2H)

Compound 71:
IR (KBr tablet):
2649, 2558, 2438, 1602, 1508, 1334, 1222, 1156 cm$^{-1}$
NMR (CDCl$_3$, δ ppm):
7.87–7.27 (m, 9H), 7.04–7.27 (m, 4H),
4.24–3.31 (m, 16H), 2.97 (s, 3H),
2.15–2.02 (m, 2H), 1.73 (bs, 2H)

Referential Example 4:

Synthesis of N-(2,3-epoxypropyl)-N-(4-methylphenyl)sulfonylaniline:

To 10 ml of dried DMF suspension of 0.48 g (12.0 mmol) of sodium hydride (60%), while stirring at a room temperature in an argon gas atmosphere, a solution obtained by adding 10 ml of the dried DMF in 2.59 g (10.5 mmol) of N-(4-methylphenyl)sulfonylaniline was added dropwise in 10 minutes, and the mixture was stirred for 30 minutes under the same conditions. To this mixture, under the same conditions, a solution obtained by adding 10 ml of the dried DMF in 1.37 (10.0 mmol) of epibromohydrin was added dropwise over 10 minutes, and the mixture was stirred for 22 hours under the same conditions. Then, the reaction liquid was poured into 200 ml of cold 0.5N sodium hydroxide and the mixture was extracted with ether (50 ml ×3). The whole ether layers were combined and washed with water (50 ml ×3) and a saturated saline solution (50 ml). After drying over anhydrous sodium sulfate, the solvent was removed from the mixture by distillation. The residue of oily substance was washed three times with n-hexane according to the decantation method and was dried under reduced pressure to obtain 2.00 g of the subject compound as an yellowish solid (Yield: 66.0%).

m.p. 75° to 78° C.

IR (KBr tablet):
1594, 1493, 1343, 1164, 1093, 1065, 863 cm$^{-1}$

NMR (CDCl$_3$, δ ppm):
2.36–2.48 (m, 1H), 2.39 (s, 3H), 2.67–2.73 (m, 1H),
3.08–3.18 (m, 1H), 3.58–3.77 (m, 2H),
7.03–7.13 (m, 2H), 7.20–7.36 (m, 5H),
7.44–7.54 (m, 2H)

Example 19:

1-[4,4-Bis(4-fluorophenyl)butyl]-4-[2-hydoxy-3-{N-(4-methylphenyl)sulfonyl-N-phenylamino }propyl]piperazine (compound 72) and its dihydrochloride (compound 73):

By using the compound obtained in Referential Example 4, subject compounds were obtained in the same manner as Example 18.

Compound 72:

oily substance

NMR (CDCl$_3$, δ ppm):
1.31–1.46 (m, 2H), 1.98 (q, 2H, J=8 Hz),
2.20–2.39 (m, 8H), 2.41 (s, 3H), 2.46–2.60 (m, 4H),
3.59 (d, 2H, J=6 Hz), 3.64–3.77 (m, 1H),
3.85 (t, 1H, J=8 Hz), 6.95 (tt, 3H, J=2.5, 9 Hz),
7.01–7.09 (m, 2H), 7.09–7.19 (m, 4H),
7.19–7.33 (m, 6H), 7.45 (d, 2H, J=8.5 Hz)

Compound 73:

white crystals m.p. 132°–136° C.

IR (KBr tablet):
3440, 3330, 3299, 2643–2437, 1625 (shoulder), 1601, 1508, 1454, 1335, 1223, 1161, 835, 823 cm$^{-1}$ NMR (DMSO-d$_6$, δ ppm):
1.55–1.77 (m, 2H), 2.05–2.2 (m, 2H),
2.49 (s, 3H), 3.00–3.95 (m, 14H),
3.95–4.05 (m, 1H), 4.11 (t, 1H, J=8 Hz),
7.10–7.27 (m, 6H), 7.27–7.57 (m, 11H)

Example 20:

In the same manner as Example 18, the following compounds were obtained.

(1) 1-[3-(N-acetyl-N-phenylamino)-2-hydroxypropyl]-4-[4,4-bis(4-fluorophenyl)butyl]piperazine (compound 74):

oily substance

NMR (CDCl$_3$, δ ppm):
1.31–1.47 (m, 2H), 1.86 (s, 3H), 1.90–2.05 (m, 2H),
2.20–2.47 (m, 10H), 2.47–2.63 (m, 2H),
3.60–4.00 (m, 4H), 6.88–7.00 (m, 4H),
7.07–7.20 (m, 4H), 7.20–7.28 (m, 2H),
7.28–7.46 (m, 3H)

(2) Dihydrochloride of compound 74 (compound 75):

white crystals m.p. 182°–185° C.

IR (KBr tablet):
3400, 3275 (shoulder), 2650–2464, 1651, 1594, 1508, 1223, 833 cm$^{-1}$ NMR (DMSO-d$_6$, δ ppm):
1.53–1.74 (m, 2H), 1.80 (s, 3H), 2.00–2.22 (m, 2H),
3.00–4.05 (m, 14H), 4.11 (t, 1H, J=8 Hz),
4.16–4.30 (m, 1H), 7.20 (t, 4H, J=9 Hz),
7.30 –7.50 (m, 5H), 7.50–7.63 (m, 4H)

(3) 1-[4,4-Bis(4-fluorophenyl)butyl]-4-[3-(N,N-diphenylamino) -2-hydroxypropyl]piperazine (compound 76):

oily substance

NMR (CDCl$_3$, δ ppm):
1.30–1.45 (m, 2H), 1.90–2.10 (q, 2H),
2.20–2.45 (m, 10H), 2.45–2.60 (m, 2H),
3.70 –3.75 (m, 2H), 3.83 (t, 1H), 3.95–4.10 (m, 1H),
6.90–7.00 (m, 6H), 7.05 (d, 4H), 7.05–7.15 (m, 4H),
7.20 (t, 4H)

(4) Dihydrochloride of compound 76 (compound 77):

white crystals m.p. 104°–112° C.

IR (KBr tablet):
3330, 2923, 2560, 2366, 1595, 1502, 1450, 1225, 1159, 832, 755, 699 cm$^{-1}$ NMR (DMSO-d$_6$, δ ppm):
1.60–1.70 (m, 2H), 1.90–2.20 (q, 2H),
3.00–3.90 (m, 14H), 4.03 (t, 1H),
4.20–4.30 (m, 1H), 6.90–7.00 (t, 2H),
7.00–7.15 (m, 8H), 7.20–7.40 (m, 8H)

(5) 1-[4,4-Bis(4-fluorophenyl)butyl]-4-[2-hydroxy-3-(N-phenyl-N-phenylmethylamino)propyl]piperazine (compound 78):

oily substance

NMR (CDCl$_3$, δ ppm):
1.30–1.50 (m, 2H), 1.90–2.05 (q, 2H),
2.20–2.50 (m, 10H), 2.50–2.70 (d, 2H),
3.85 (t, 1H), 4.00–4.10 (m, 1H), 4.66 (d, 2H),
6.65–6.80 (m, 3H), 6.90–7.00 (m, 4H),
7.00–7.30 (m, 11H)

(6) Trihydrochloride of compound 78 (compound 79):

white crystals m.p. 112°–118° C.

IR (KBr tablet):
3554, 3411, 2565, 1602, 1506, 1225, 832 cm$^{-1}$

NMR (DMSO-d$_6$, δ ppm):
1.50–1.70 (m, 2H), 2.00–2.15 (m, 2H),
3.00–3.90 (m, 14H), 4.03 (t, 1H),
4.40–4.50 (m, 1H), 4.67 (s, 2H), 6.62 (t, 1H),
6.79 (d, 2H), 7.00–7.40 (m, 15H)

(7) 1-[4,4-Bis(4-fluorophenyl)butyl]-4-[3-(N-ethoxycarbonyl-N-phenylamino)-2-hydroxypropyl ]piperazine (compound 80):

oily substance

NMR (CDCl$_3$, δ ppm):

1.1–1.3 (t, 3H, J=6.9 Hz), 1.3–1.5 (m, 2H),
1.9–2.1 (q, 2H), 2.2–2.7 (m, 14H),
3.5–4.0 (m, 2H), 4.14 (q, 2H, J=6.9 Hz),
6.9–7.5 (m, 13H)

(8) Dihydrochloride of compound 80 (compound 81):
white crystals
IR (KBr tablet):
3420, 2560, 1510, 1220, 1160, 830 cm$^{-1}$
NMR (DMSO-d$_6$, δ ppm:
1.1–1.3 (t, 3H, J=6.9 Hz), 1.6–1.8 (m, 2H),
2.1–2.2 (q, 2H, J=7.6 Hz), 2.9–3.9 (m, 14H),
4.1–4.3 (m, 4H), 7.1–7.5 (m, 13H)

Example 21:

In the same manner as Examples 11 and 12, the following compounds were obtained.

(1) 1-[4,4-Bis(4-fluorophenyl)butyl]-4-[2-benzoxy-3-phenylthiopropyl]piperazine (compound 82):
oily substance
NMR (CDCl$_3$, δ ppm):
1.4–1.5 (m, 2H), 1.9–2.0 (m, 2H),
2.3–2.6 (m, 12H), 3.6–3.7 (m, 1H),
3.86 (t, 1H, J=7.8 Hz), 4.59 (d, 2H, J=3.0 Hz),
6.9–7.0 (m, 4H), 7.1–7.2 (m, 5H),
7.2–7.4 (m, 9H)

(2) Dihydrochloride of compound 82 (compound 83):
white crystals
m.p. 84°–86° C.
IR (KBr tablet):
3440, 2930, 2550, 2450. 1510, 1220, 1060, 840 cm$^{-1}$
NMR (DMSO-d$_6$, δ ppm):
1.6–1.7 (m, 2H), 2.1–2.2 (m, 2H),
3.2–3.8 (m, 14H), 4.0–4.1 (m, 1H),
4.3–4.4 (m, 1H), 4.6–4.7 (s, 2H),
7.1–7.2 (m, 4H), 7.4–7.6 (m, 14H)

(3) 1-[4,4-Bis(4-fluorophenyl)butyl]-4-[2-ethoxycarbonylmethoxy-3-phenylthiopropyl]piperazine (compound 84):
oily substance
IR (KBr tablet):
3410, 2940, 1740, 1510, 1280, 1160, 830 cm$^{-1}$
NMR (CDCl$_3$, δ ppm):
1.28 t, 3H, J=7.6 Hz), 1.3–1.5 (m, 2H),
1.9–2.0 (m, 2H), 2.3–2.7 (m, 12H),
3.1–3.2 (m, 1H), 3.63 (t, 1H, J=5.9 Hz),
3.85 (t, 1H, J=7.8 Hz), 4.17 (q, 2H, J=7.6 Hz),
4.24 (s, 2H), 6.9–7.0 (m, 3H), 7.1–7.2 (m, 4H),
7.2–7.3 (m, 2H), 7.3–7.5 (m, 4H)

Example 22:

Sodium 1-phenylthiomethyl-2-[4-{4,4-bis(4-fluorophenyl)butyl}piperazin]ethoxyacetate (compound 85):

0.05 g (0.88 mmol) of 1-[4,4-bis(4-fluorophenyl)butyl]-4-[2-ethoxycarbonylmethoxy-3-phenylthiopropyl]piperazine was dissolved in 10 ml of methanol, and 1.75 ml of 2.0N sodium hydroxide solution was added to the mixture. After the air was replaced with argon gas, the mixture was stirred for 2 hours at a room temperature. The reaction liquid was poured in 50 ml of distilled water and neutralized by dilute hydrochloric acid, and then the mixture was extracted by benzene.

After drying over anhydrous sodium sulfate, the solvent was removed from the mixture by distillation under reduced pressure, and the residue was separated by column chromatography (silica gel, CHCl$_3$: MeOH=97:3). The product was dissolved in 20 ml of benzene, and after washing with a saturated sodium carbonate, the mixture was dried. The solvent was removed from the mixture by distillation to obtain 220 mg of a subject compound in an oily material (yield: 46%).
NMR (CDCl$_3$, δ ppm):
1.3–1.4 (m, 2H), 1.9–2.0 (m, 2H),
2.40 (t, J=7.6 Hz, 2H), 2.6–3.1 (m, 12H),
3.6–3.7 (m, 1H), 3.84 (t, 1H, J=7.8 Hz),
4.07 (ABq, 2H, J=17.3 Hz), 6.9–7.0 (m, 4H),
7.1–7.2 (m, 4H), 7.2–7.3 (m, 5H)

Test Example 1:

Antagonism against calcium:

A test for antagonism against calcium of a diphenylpiperazine derivative according to the present invention and furnarizine was carried out as follows.

Male Wistar rats (300–350g) were exsanguinated to death and submitted to thoracotomy to take off aortae. Ring specimens having a width of 3 to 4 mm were prepared from the aortae. The specimen was suspended in a Magnus tube which was filled with Krebs Henseleit liquid of 37°±0.5° C., aerated with a mixing gas (95% of O$_2$ and 5% of CO$_2$) flowing in the liquid. A load of approximately 2 g was given to the specimen, and a tension variation was isometrically recorded.

The calcium antagonism was indicated by the concentration (M) of a testing agent which inhibits 50% of the maximum contraction of concentration-dependent-contraction (10–60 mM) of KCl, and the results were shown in Table 1.

Test Example 2:

After female and male crossbred adult dogs were put under anesthesia by using pentobarbital-Na, a cannula for blood pressure measuring and a cannula for drug dosing were set to the femoral artery and the femoral vein, respectively. The blood flow was measured using a probe fixed to the vertebral artery.

The drug was administered in order within a range of 10 to 300 (μg/kg,i.v.) for compounds according to the present invention and 30 to 1000 (μg/kg,i.v.) for furnarizine. The variation of the blood flow amount was shown in Table 2.

TABLE 1

| Compound No. | 50% inhibitory concentration (M) |
|---|---|
| 3 | 1.3 × 10$^{-6}$ |
| 4 | 1.3 × 10$^{-6}$ |
| 5 | 1.2 × 10$^{-6}$ |
| 6 | 2.2 × 10$^{-7}$ |
| 10 | 1.6 × 10$^{-7}$ |
| 12 | 2.0 × 10$^{-7}$ |
| 14 | 2.8 × 10$^{-7}$ |
| 16 | 1.0 × 10$^{-7}$ |
| 18 | 1.3 × 10$^{-7}$ |
| 20 | 2.7 × 10$^{-7}$ |
| 22 | 6.3 × 10$^{-7}$ |
| 24 | 1.4 × 10$^{-6}$ |
| 28 | 1.1 × 10$^{-7}$ |
| 31 | 1.1 × 10$^{-6}$ |
| 35 | 1.6 × 10$^{-7}$ |
| 37 | 1.4 × 10$^{-7}$ |
| 39 | 3.4 × 10$^{-7}$ |
| 41 | 4.3 × 10$^{-7}$ |
| 43 | 2.8 × 10$^{-7}$ |
| 45 | 1.1 × 10$^{-6}$ |
| 47 | 6.9 × 10$^{-7}$ |
| 51 | 1.4 × 10$^{-7}$ |
| 53 | 1.2 × 10$^{-6}$ |
| 55 | 1.3 × 10$^{-6}$ |
| 57 | 3.4 × 10$^{-7}$ |
| Furnarizine | 1.6 × 10$^{-6}$ |

Test Example 3:

Acute toxicity:

An acute toxicity test for the diphenylpiperazine derivatives of the present invention obtained in the above-described Examples was carried out as follows.

Male ICR mice of 4 week old were bought, and after approximately 10 days preliminary breeding, the mice were provided for the test. The mice were fasted for 16 hours from the day before the test. The testing drugs were dissolved in soybean oil, in an amount of 0.2 ml drug per 10 g of the weight of a mouse, and a compulsory oral dosing was conducted by using a metal stomach probe. For the control group, only soybean oil was given. The observation period after the dosing was 14 days, and from the survival rate after the 14 days, the $LD_{50}$ value was calculated according to the Richfield-Wilcoxon method.

As a result, for all diphenylpiperazine derivatives of the present invention indicated $LD_{50}$ value of more than 1000 mg/kg.

TABLE 2

| Compound | Concentration (μg/kg, i.v.) | Variation (%) |
|---|---|---|
| 10 | 10 | 18 |
|  | 30 | 14 |
|  | 100 | 80 |
|  | 300 | 125 |
| 35 | 10 | 13 |
|  | 30 | 26 |
|  | 100 | 66 |
|  | 300 | 87 |
| 43 | 10 | 7 |
|  | 30 | 15 |
|  | 100 | 55 |
|  | 300 | 131 |
| 41 | 10 | 12 |
|  | 30 | 25 |
|  | 100 | 66 |
|  | 300 | 87 |
| Furnarizine | 30 | 8 |
|  | 100 | 27 |
|  | 300 | 44 |
|  | 1000 | 55 |

Preparation Example 1:

| Compound 1 | 24.0 g |
|---|---|
| Milk sugar | 151.1 g |
| Hydroxypropylcellulose | 4.9 g |
| Corn starch | 20.0 g |
| Total | 200.0 g |

Compound 1, milk sugar and corn starch were screened through a sieve of #60, and after mixing uniformly, the mixture was put in a kneader. A solution of hydroxypropyl-cellulose was added to the kneader, and the mixture was kneaded. Then, the mixture was sieved through a sieve of #18 and was dried with air blow at 50° C. After drying the mixture, the particle size of the mixture was regulated to give a granule, and 500 mg of granule was wrapped in each wrapper.

Preparation Example 2:

| Compound 2 | 60.0 g |
|---|---|
| Milk sugar | 118.5 g |
| Corn starch | 20.0 g |
| Talc | 1.5 g |
| Total | 200.0 g |

The components were finely powdered, and after sufficiently mixed to give a uniform mixture, the mixture was put in gelatin capsules for oral use, each capsule containing 0.2 g mixture.

Preparation Example 3:

| Compound 3 | 24.0 g |
|---|---|
| Milk sugar | 113.1 g |
| Corn starch | 20.0 g |
| Hydroxypropylcellulose | 4.9 g |
| Magnesium stearate | 2.0 g |
| Total | 200.0 g |

Compound 3, milk sugar and corn starch were screened through a sieve of #60, and after mixing uniformly, the mixture was put in a kneader. A solution of hydroxypropyl-cellulose was added to the kneader, and the mixture was kneaded. Then, the mixture was dried with air blow at 50° C. After drying the mixture, the particle size of the mixture was regulated through a sieve of #16, and then magnesium stearate was added and uniformly mixed. The mixture was processed by a tableting machine to obtain a tablet having a weight of 200 mg and a diameter of 8 mm.

Preparation Example 4:

| Compound 16 | 6.0 g |
|---|---|
| Witepsole (H-15) | 72.0 g |
| Witepsole (E-75) | 72.0 g |
| Total | 150.0 g |

Witepsole (H-15) and Witepsole (E-75) were mixed and melted at 50°-60° C., and, while stirring, this mixture was gradually added to a fine powdery compound 16 which was previously ground and mixed within a mortar. The mixture was sufficiently mixed to be uniform. The mixture was injected in suppository molds so that each contained 1.5 g mixture and the mold was air-cooled at room temperature for solidification to give suppositories.

Preparation Example 5:

| Compound 28 | 1.0 g |
|---|---|
| 0.1 N hydrochloric acid | 10.0 ml |
| Benzyl alcohol | 30.0 ml |
| Distilled water for injection | balance |
| Total | 1000.0 ml |

To 400 ml of distilled water for injection, 10 ml of 0.1N hydrochloric acid was added, and compound 28 was dissolved in the mixture. To this solution, 30 ml of benzyl alcohol and suitable amount of the distilled water for injection were added. pH of the solution was adjusted to 3.0 with NaOH, and the total amount of the solution was adjusted to 1000 ml. The obtained solution was filled in ampuls of 10 ml, and autoclaving of the ampuls was carried out to obtain an injection.

Industrial Applicability:

The diphenylpiperazine derivatives according to the present invention possess excellent calcium antagonism and less side effect. Hence, drugs for circulatory organs, containing the diphenylpiperazine derivative as an active ingredient, are quite useful for the cure and prevention of a variety of circulatory organ diseases such as hypertension, angina pectoris, cerebral circulatory disturbances, arrhythmia, and the like.

We claim:

1. A diphenylpiperazine compound represented by the following formula (1) or pharmaceutically acceptable salts thereof:

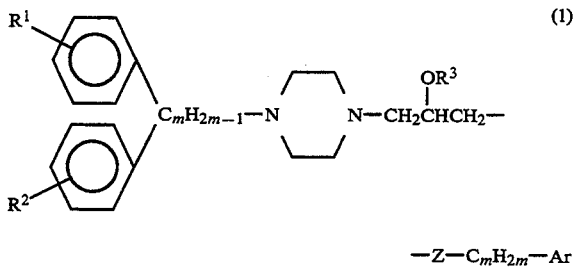

wherein, $R^1$ and $R^2$ are the same or different and independently represent a hydrogen atom, a halogen atom, an alkyl group, an alkoxy group, a nitro group, an amino group, a hydroxy group, a carboxyl group, an esterified carboxyl group or a trifluoromethyl group; $R^3$ represents a hydrogen atom, an alkyl group, an aralkyl group, an acyl group, a nitro group, a carboxymethyl group, or an esterified carboxymethyl group; Ar represents a phenyl or naphthyl group which may have 1 to 3 substituents selected from the group consisting of halogen, alkyl, alkoxy, aryloxy, aralkyloxy, nitro, an amino, cyano, acyl, hydroxy, carboxyl, esterified carboxyl, methanesulfonyl, p-toluenesulfonyl, aryl or trifluoromethyl; Z represents a group of $-NR^4-$, wherein $R^4$ represents a hydrogen atom, an alkyl group, an aralkyl group, an acyl group, an aryl group, a methanesulfonyl group, a p-toluenesulfonyl group, a carboxyl group, or an esterified carboxyl group; m represents a number of 1 to 5; and n represents a number of 0 to 5; with the proviso that the alkyl group has 1-10 carbon atoms; the alkoxyl group has 1-8 carbon atoms; the aralkyl group is selected from the group consisting of benzyl, phenylethyl, methylbenzyl, and naphthylmethyl; the aryl group is a phenyl group or a phenyl group having one or more substituents selected from the group consisting of halogen, alkyl, alkoxyl, hydroxy and amino; and the acyl group is an acetyl, propionyl, butyryl, benzoyl, halogenobenzoyl or alkoxybenzoyl group.

2. The diphenylpiperazine compound or pharmaceutically acceptable salts thereof as defined in claim 1, wherein $R^1$ and $R^2$ are hydrogen and halogen and $R^3$ is selected from the group consisting of hydrogen, $C_{1-10}$ alkyl, acetyl, propionyl, butyryl, nitro and benzyl groups.

3. The diphenylpiperazine compound or pharmaceutically acceptable salts thereof as defined in claim 2 wherein $R^3$ is hydrogen.

4. The pharmaceutically acceptable diphenylpiperazine salt as defined in claim 1, wherein the salt is selected from the group consisting of acid addition salts and quaternary ammonium salts.

5. The diphenylpiperazine compound or pharmaceutically acceptable salts thereof, selected from the group consisting of:
 1-[4,4-bis(4-fluorophenyl)butyl]-4-(2-hydroxy-3-phenylaminopropyl]piperazine,
 1-[4,4-bis(4-fluorophenyl)butyl]-4-[2-hydroxy-3-(4-methylphenylamino)propyl]piperazine,
 1-[4,4-bis(4-fluorophenyl)butyl]-4-[3-(4-fluorophenylamino)-2-hydroxypropyl]piperazine,
 1-[4,4-bis(4-fluorophenyl)butyl]-4-[2-hydroxy-3-(4-hydroxyphenylamino)propyl]piperazine, and
 1-[4,4-bis(4-fluorophenyl)butyl]-4-[2-hydroxy-3-(4-methoxyphenylamino)propyl]piperazine.

6. A pharmaceutical composition for the treatment of circulatory organs comprising the diphenylpiperazine compound of claim 1, or a pharmaceutically acceptable salt thereof, and a pharmaceutically accentable carrier.

7. The pharmaceutical composition of claim 6 wherein the composition is in a form selected from the group consisting of powder, granule, tablet, capsule, solution and injectable forms.

8. A method for the treatment of hypertension, angina pectoris, arrhythmia and disturbance of cerebral circulation, comprising administering to an animal or human subject an effective amount of the pharmaceutical composition of claim 6.

9. The method of claim 8 comprising administering to the animal or human subject an oral dose of the pharmaceutical composition in the amount of 10 to 1000 mg per day.

* * * * *

UNITED STATES PATENT AND TRADEMARK OFFICE
CERTIFICATE OF CORRECTION

PATENT NO. : 5,391,552
DATED : June 21, 1995
INVENTOR(S) : INAZU et al.

It is certified that error appears in the above-identified patent and that said Letters Patent is hereby corrected as shown below:

Column 29, line 16, in formula 1, "-Z-$C_mH_{2m}$-Ar" should read -- -Z-$C_nH_{2n}$-Ar--.

Signed and Sealed this

Twenty-fifth Day of August, 1998

*Attest:*

BRUCE LEHMAN

*Attesting Officer*  *Commissioner of Patents and Trademarks*